United States Patent
Presnell et al.

(10) Patent No.: US 7,517,958 B2
(45) Date of Patent: Apr. 14, 2009

(54) INTERLEUKIN-17 RECEPTOR HOMOLOGUE

(75) Inventors: Scott R. Presnell, Tacoma, WA (US); Steven K. Burkhead, Hershey, PA (US); Sarah L. Pownder, Kirkland, WA (US)

(73) Assignee: ZymoGenetics, Inc., Seattle, WA (US)

( * ) Notice: Subject to any disclaimer, the term of this patent is extended or adjusted under 35 U.S.C. 154(b) by 89 days.

(21) Appl. No.: 11/537,916

(22) Filed: Oct. 2, 2006

(65) Prior Publication Data

US 2007/0048824 A1 Mar. 1, 2007

Related U.S. Application Data

(63) Continuation of application No. 10/458,647, filed on Jun. 10, 2003, now abandoned, which is a continuation of application No. 09/608,918, filed on Jun. 30, 2000, now abandoned.

(60) Provisional application No. 60/142,555, filed on Jul. 7, 1999.

(51) Int. Cl.
*C07K 14/00* (2006.01)
(52) U.S. Cl. .................... 530/350; 530/387.3; 530/351; 435/69.7; 514/2
(58) Field of Classification Search ........................ None
See application file for complete search history.

(56) References Cited

U.S. PATENT DOCUMENTS

2002/0177188 A1* 11/2002 Chen et al. ................. 435/69.1

FOREIGN PATENT DOCUMENTS

| WO | WO 98/37193 | 8/1998 |
| WO | WO 98/49307 | 11/1998 |
| WO | WO 99/07848 | 2/1999 |

OTHER PUBLICATIONS

S. Vukicevic et al. Induction of nephrogenic mesenchyme by osteogenic protein 1 (bone morphogenetic protein 7). 1996. Proc. Natl. Acad. Sci. USA, 93: 9021-26.*
P. Parnet et al. IL-1Rrp is a novel receptor-like molecule similar to the type I interleukin-1 receptor and its homologous T1/ST2 and IL-1R AcP. 1996. J. Biol. Chem., 271(8): 3967-70.*
Yan et al., "Two-amino acid molecular switch in an epithelial morphogen that regulates binding to two distinct receptors," *Science* 290:523-527, 2000.
Sequence from Incyte Pharmaceuticals, Inc., (No. INC5424219).
Zabarovsky,E. et al., *H. sapiens* DNA sequence (HSDNASFAR; Accession No. Z22384).
Zabarovsky,E. et al., *H. sapiens* DNA sequence (HSDNASFAH; Accession No. Z22374).

* cited by examiner

*Primary Examiner*—Dong Jiang
(74) *Attorney, Agent, or Firm*—Nicholas V. Sherbina

(57) ABSTRACT

Cytokines and their receptors have proven usefulness in both basic research and as therapeutics. The present invention provides a new human cytokine receptor designated as "Zcytor14."

7 Claims, No Drawings

SEQUENCE LISTING

<160> NUMBER OF SEQ ID NOS: 12

<210> SEQ ID NO 1
<211> LENGTH: 2255
<212> TYPE: DNA
<213> ORGANISM: Homo sapiens
<220> FEATURE:
<221> NAME/KEY: CDS
<222> LOCATION: (154)...(2229)

<400> SEQUENCE: 1

```
aactacccag cacagccccc tccgcccccct ctggaggctg aagagggatt ccagcccctg      60
ccacccacag acacgggctg actggggtgt ctgccccccct tggggggggg cagcacaggg     120
cctcaggcct gggtgccacc tggcacctag aag atg cct gtg ccc tgg ttc ttg      174
                                    Met Pro Val Pro Trp Phe Leu
                                      1               5 ctg tcc ttg gca ctg ggc cga agc cca gtg gtc ctt tct ctg gag agg       222
Leu Ser Leu Ala Leu Gly Arg Ser Pro Val Val Leu Ser Leu Glu Arg
         10                  15                  20 ctt gtg ggg cct cag gac gct acc cac tgc tct ccg ggc ctc tcc tgc       270
Leu Val Gly Pro Gln Asp Ala Thr His Cys Ser Pro Gly Leu Ser Cys
 25                  30                  35 cgc ctc tgg gac agt gac ata ctc tgc ctg cct ggg gac atc gtg cct       318
Arg Leu Trp Asp Ser Asp Ile Leu Cys Leu Pro Gly Asp Ile Val Pro
 40                  45                  50                  55 gct ccg ggc ccc gtg ctg gcg cct acg cac ctg cag aca gag ctg gtg       366
Ala Pro Gly Pro Val Leu Ala Pro Thr His Leu Gln Thr Glu Leu Val
                 60                  65                  70 ctg agg tgc cag aag gag acc gac tgt gac ctc tgt ctg cgt gtg gct       414
Leu Arg Cys Gln Lys Glu Thr Asp Cys Asp Leu Cys Leu Arg Val Ala
             75                  80                  85 gtc cac ttg gcc gtg cat ggg cac tgg gaa gag cct gaa gat gag gaa       462
Val His Leu Ala Val His Gly His Trp Glu Glu Pro Glu Asp Glu Glu
         90                  95                 100 aag ttt gga gga gca gct gac tca ggg gtg gag gag cct agg aat gcc       510
Lys Phe Gly Gly Ala Ala Asp Ser Gly Val Glu Glu Pro Arg Asn Ala
    105                 110                 115 tct ctc cag gcc caa gtc gtg ctc tcc ttc cag gcc tac cct act gcc       558
Ser Leu Gln Ala Gln Val Val Leu Ser Phe Gln Ala Tyr Pro Thr Ala
120                 125                 130                 135 cgc tgc gtc ctg ctg gag gtg caa gtg cct gct gcc ctt gtg cag ttt       606
Arg Cys Val Leu Leu Glu Val Gln Val Pro Ala Ala Leu Val Gln Phe
                140                 145                 150 ggt cag tct gtg ggc tct gtg gta tat gac tgc ttc gag gct gcc cta       654
Gly Gln Ser Val Gly Ser Val Val Tyr Asp Cys Phe Glu Ala Ala Leu
            155                 160                 165 ggg agt gag gta cga atc tgg tcc tat act cag ccc agg tac gag aag       702
Gly Ser Glu Val Arg Ile Trp Ser Tyr Thr Gln Pro Arg Tyr Glu Lys
        170                 175                 180 gaa ctc aac cac aca cag cag ctg cct gcc ctg ccc tgg ctc aac gtg       750
Glu Leu Asn His Thr Gln Gln Leu Pro Ala Leu Pro Trp Leu Asn Val
    185                 190                 195 tca gca gat ggt gac aac gtg cat ctg gtt ctg aat gtc tct gag gag       798
Ser Ala Asp Gly Asp Asn Val His Leu Val Leu Asn Val Ser Glu Glu
200                 205                 210                 215 cag cac ttc ggc ctc tcc ctg tac tgg aat cag gtc cag ggc ccc cca       846
Gln His Phe Gly Leu Ser Leu Tyr Trp Asn Gln Val Gln Gly Pro Pro
                220                 225                 230
```

-continued

| | |
|---|---|
| aaa ccc cgg tgg cac aaa aac ctg act gga ccg cag atc att acc ttg<br>Lys Pro Arg Trp His Lys Asn Leu Thr Gly Pro Gln Ile Ile Thr Leu<br>235 240 245 | 894 |
| aac cac aca gac ctg gtt ccc tgc ctc tgt att cag gtg tgg cct ctg<br>Asn His Thr Asp Leu Val Pro Cys Leu Cys Ile Gln Val Trp Pro Leu<br>250 255 260 | 942 |
| gaa cct gac tcc gtt agg acg aac atc tgc ccc ttc agg gag gac ccc<br>Glu Pro Asp Ser Val Arg Thr Asn Ile Cys Pro Phe Arg Glu Asp Pro<br>265 270 275 | 990 |
| cgc gca cac cag aac ctc tgg caa gcc gcc cga ctg cga ctg ctg acc<br>Arg Ala His Gln Asn Leu Trp Gln Ala Ala Arg Leu Arg Leu Leu Thr<br>280 285 290 295 | 1038 |
| ctg cag agc tgg ctg ctg gac gca ccg tgc tcg ctg ccc gca gaa gcg<br>Leu Gln Ser Trp Leu Leu Asp Ala Pro Cys Ser Leu Pro Ala Glu Ala<br>300 305 310 | 1086 |
| gca ctg tgc tgg cgg gct ccg ggt ggg gac ccc tgc cag cca ctg gtc<br>Ala Leu Cys Trp Arg Ala Pro Gly Gly Asp Pro Cys Gln Pro Leu Val<br>315 320 325 | 1134 |
| cca ccg ctt tcc tgg gag aac gtc act gtg gac aag gtt ctc gag ttc<br>Pro Pro Leu Ser Trp Glu Asn Val Thr Val Asp Lys Val Leu Glu Phe<br>330 335 340 | 1182 |
| cca ttg ctg aaa ggc cac cct aac ctc tgt gtt cag gtg aac agc tcg<br>Pro Leu Leu Lys Gly His Pro Asn Leu Cys Val Gln Val Asn Ser Ser<br>345 350 355 | 1230 |
| gag aag ctg cag ctg cag gag tgc ttg tgg gct gac tcc ctg ggg cct<br>Glu Lys Leu Gln Leu Gln Glu Cys Leu Trp Ala Asp Ser Leu Gly Pro<br>360 365 370 375 | 1278 |
| ctc aaa gac gat gtg cta ctg ttg gag aca cga ggc ccc cag gac aac<br>Leu Lys Asp Asp Val Leu Leu Leu Glu Thr Arg Gly Pro Gln Asp Asn<br>380 385 390 | 1326 |
| aga tcc ctc tgt gcc ttg gaa ccc agt ggc tgt act tca cta ccc agc<br>Arg Ser Leu Cys Ala Leu Glu Pro Ser Gly Cys Thr Ser Leu Pro Ser<br>395 400 405 | 1374 |
| aaa gcc tcc acg agg gca gct cgc ctt gga gag tac tta cta caa gac<br>Lys Ala Ser Thr Arg Ala Ala Arg Leu Gly Glu Tyr Leu Leu Gln Asp<br>410 415 420 | 1422 |
| ctg cag tca ggc cag tgt ctg cag cta tgg gac gat gac ttg gga gcg<br>Leu Gln Ser Gly Gln Cys Leu Gln Leu Trp Asp Asp Asp Leu Gly Ala<br>425 430 435 | 1470 |
| cta tgg gcc tgc ccc atg gac aaa tac atc cac aag cgc tgg gcc ctc<br>Leu Trp Ala Cys Pro Met Asp Lys Tyr Ile His Lys Arg Trp Ala Leu<br>440 445 450 455 | 1518 |
| gtg tgg ctg gcc tgc cta ctc ttt gcc gct gcg ctt tcc ctc atc ctc<br>Val Trp Leu Ala Cys Leu Leu Phe Ala Ala Ala Leu Ser Leu Ile Leu<br>460 465 470 | 1566 |
| ctt ctc aaa aag gat cac gcg aaa gcg gcc gcc agg ggc cgc gcg gct<br>Leu Leu Lys Lys Asp His Ala Lys Ala Ala Ala Arg Gly Arg Ala Ala<br>475 480 485 | 1614 |
| ctg ctc ctc tac tca gcc gat gac tcg ggt ttc gag cgc ctg gtg ggc<br>Leu Leu Leu Tyr Ser Ala Asp Asp Ser Gly Phe Glu Arg Leu Val Gly<br>490 495 500 | 1662 |
| gcc ctg gcg tcg gcc ctg tgc cag ctg ccg ctg cgc gtg gcc gta gac<br>Ala Leu Ala Ser Ala Leu Cys Gln Leu Pro Leu Arg Val Ala Val Asp<br>505 510 515 | 1710 |
| ctg tgg agc cgt cgt gaa ctg agc gcg cag ggg ccc gtg gct tgg ttt<br>Leu Trp Ser Arg Arg Glu Leu Ser Ala Gln Gly Pro Val Ala Trp Phe<br>520 525 530 535 | 1758 |
| cac gcg cag cgg cgc cag acc ctg cag gag ggc ggc gtg gtg gtc ttg<br>His Ala Gln Arg Arg Gln Thr Leu Gln Glu Gly Gly Val Val Val Leu<br>540 545 550 | 1806 |

-continued

| | | |
|---|---|---|
| ctc ttc tct ccc ggt gcg gtg gcg ctg tgc agc gag tgg cta cag gat<br>Leu Phe Ser Pro Gly Ala Val Ala Leu Cys Ser Glu Trp Leu Gln Asp<br>555                               560                          565 | 1854 |
| ggg gtg tcc ggg ccc ggg gcg cac ggc ccg cac gac gcc ttc cgc gcc<br>Gly Val Ser Gly Pro Gly Ala His Gly Pro His Asp Ala Phe Arg Ala<br>    570                           575                           580 | 1902 |
| tcg ctc agc tgc gtg ctg ccc gac ttc ttg cag ggc cgg gcg ccc ggc<br>Ser Leu Ser Cys Val Leu Pro Asp Phe Leu Gln Gly Arg Ala Pro Gly<br>585                               590                          595 | 1950 |
| agc tac gtg ggg gcc tgc ttc gac agg ctg ctc cac ccg gac gcc gta<br>Ser Tyr Val Gly Ala Cys Phe Asp Arg Leu Leu His Pro Asp Ala Val<br>600                         605                         610                         615 | 1998 |
| ccc gcc ctt ttc cgc acc gtg ccc gtc ttc aca ctg ccc tcc caa ctg<br>Pro Ala Leu Phe Arg Thr Val Pro Val Phe Thr Leu Pro Ser Gln Leu<br>                      620                         625                         630 | 2046 |
| cca gac ttc ctg ggg gcc ctg cag cag cct cgc gcc ccg cgt tcc ggg<br>Pro Asp Phe Leu Gly Ala Leu Gln Gln Pro Arg Ala Pro Arg Ser Gly<br>                    635                          640                        645 | 2094 |
| cgg ctc caa gag aga gcg gag caa gtg tcc cgg gcc ctt cag cca gcc<br>Arg Leu Gln Glu Arg Ala Glu Gln Val Ser Arg Ala Leu Gln Pro Ala<br>650                             655                         660 | 2142 |
| ctg gat agc tac ttc cat ccc ccg ggg act ccc gcg ccg gga cgc ggg<br>Leu Asp Ser Tyr Phe His Pro Pro Gly Thr Pro Ala Pro Gly Arg Gly<br>665                               670                         675 | 2190 |
| gtg gga cca ggg gcg gga cct ggg gcg ggg gac ggg act taaataaagg<br>Val Gly Pro Gly Ala Gly Pro Gly Ala Gly Asp Gly Thr<br>680                             685                         690 | 2239 |
| cagacgctgt ttttct | 2255 |

<210> SEQ ID NO 2
<211> LENGTH: 692
<212> TYPE: PRT
<213> ORGANISM: Homo sapiens

<400> SEQUENCE: 2

Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

```
Thr Gln Pro Arg Tyr Glu Lys Glu Leu Asn His Thr Gln Leu Pro
            180                 185                 190
Ala Leu Pro Trp Leu Asn Val Ser Ala Asp Gly Asp Asn Val His Leu
            195                 200                 205
Val Leu Asn Val Ser Glu Glu Gln His Phe Gly Leu Ser Leu Tyr Trp
            210                 215                 220
Asn Gln Val Gln Gly Pro Pro Lys Pro Arg Trp His Lys Asn Leu Thr
225                 230                 235                 240
Gly Pro Gln Ile Ile Thr Leu Asn His Thr Asp Leu Val Pro Cys Leu
                245                 250                 255
Cys Ile Gln Val Trp Pro Leu Glu Pro Asp Ser Val Arg Thr Asn Ile
                260                 265                 270
Cys Pro Phe Arg Glu Asp Pro Arg Ala His Gln Asn Leu Trp Gln Ala
                275                 280                 285
Ala Arg Leu Arg Leu Leu Thr Leu Gln Ser Trp Leu Leu Asp Ala Pro
                290                 295                 300
Cys Ser Leu Pro Ala Glu Ala Ala Leu Cys Trp Arg Ala Pro Gly Gly
305                 310                 315                 320
Asp Pro Cys Gln Pro Leu Val Pro Pro Leu Ser Trp Glu Asn Val Thr
                325                 330                 335
Val Asp Lys Val Leu Glu Phe Pro Leu Leu Lys Gly His Pro Asn Leu
                340                 345                 350
Cys Val Gln Val Asn Ser Ser Glu Lys Leu Gln Leu Gln Glu Cys Leu
                355                 360                 365
Trp Ala Asp Ser Leu Gly Pro Leu Lys Asp Asp Val Leu Leu Leu Glu
                370                 375                 380
Thr Arg Gly Pro Gln Asp Asn Arg Ser Leu Cys Ala Leu Glu Pro Ser
385                 390                 395                 400
Gly Cys Thr Ser Leu Pro Ser Lys Ala Ser Thr Arg Ala Ala Arg Leu
                405                 410                 415
Gly Glu Tyr Leu Leu Gln Asp Leu Gln Ser Gly Gln Cys Leu Gln Leu
                420                 425                 430
Trp Asp Asp Asp Leu Gly Ala Leu Trp Ala Cys Pro Met Asp Lys Tyr
                435                 440                 445
Ile His Lys Arg Trp Ala Leu Val Trp Leu Ala Cys Leu Leu Phe Ala
                450                 455                 460
Ala Ala Leu Ser Leu Ile Leu Leu Leu Lys Lys Asp His Ala Lys Ala
465                 470                 475                 480
Ala Ala Arg Gly Arg Ala Ala Leu Leu Leu Tyr Ser Ala Asp Asp Ser
                485                 490                 495
Gly Phe Glu Arg Leu Val Gly Ala Leu Ala Ser Ala Leu Cys Gln Leu
                500                 505                 510
Pro Leu Arg Val Ala Val Asp Leu Trp Ser Arg Arg Glu Leu Ser Ala
                515                 520                 525
Gln Gly Pro Val Ala Trp Phe His Ala Gln Arg Arg Gln Thr Leu Gln
                530                 535                 540
Glu Gly Gly Val Val Val Leu Leu Phe Ser Pro Gly Ala Val Ala Leu
545                 550                 555                 560
Cys Ser Glu Trp Leu Gln Asp Gly Val Ser Gly Pro Gly Ala His Gly
                565                 570                 575
Pro His Asp Ala Phe Arg Ala Ser Leu Ser Cys Val Leu Pro Asp Phe
                580                 585                 590
```

```
Leu Gln Gly Arg Ala Pro Gly Ser Tyr Val Gly Ala Cys Phe Asp Arg
        595                 600                 605

Leu Leu His Pro Asp Ala Val Pro Ala Leu Phe Arg Thr Val Pro Val
    610                 615                 620

Phe Thr Leu Pro Ser Gln Leu Pro Asp Phe Leu Gly Ala Leu Gln Gln
625                 630                 635                 640

Pro Arg Ala Pro Arg Ser Gly Arg Leu Gln Glu Arg Ala Glu Gln Val
                645                 650                 655

Ser Arg Ala Leu Gln Pro Ala Leu Asp Ser Tyr Phe His Pro Pro Gly
            660                 665                 670

Thr Pro Ala Pro Gly Arg Gly Val Gly Pro Gly Ala Gly Pro Gly Ala
        675                 680                 685

Gly Asp Gly Thr
    690

<210> SEQ ID NO 3
<211> LENGTH: 2076
<212> TYPE: DNA
<213> ORGANISM: Artificial Sequence
<220> FEATURE:
<223> OTHER INFORMATION: This degenerate sequence encodes the amino acid
      sequence of SEQ ID NO:2.
<220> FEATURE:
<221> NAME/KEY: variation
<222> LOCATION: (1)...(2076)
<223> OTHER INFORMATION: N is any nucleotide
<220> FEATURE:
<221> NAME/KEY: misc_feature
<222> LOCATION: (1)...(2076)
<223> OTHER INFORMATION: n = A,T,C or G

<400> SEQUENCE: 3
atgccngtnc cntggttyyt nytnwsnytn gcnytnggnm gnwsnccngt ngtnytnwsn      60
ytngarmgny tngtnggncc ncargaygcn acncaytgyw snccnggnyt nwsntgymgn     120
ytntgggayw sngayathyt ntgyytnccn ggngayathg tnccngcncc nggnccngtn     180
ytngcnccna cncayytnca racngarytn gtnytnmgnt gycaraarga racngaytgy     240
gayytntgyy tnmgngtngc ngtncayytn gcngtncayg gncaytggga rgarccngar     300
gaygargara arttyggngg ngcngcngay wsnggngtng argarccnmg naaygcnwsn     360
ytncargcnc argtngtnyt nwsnttycar gcntayccna cngcnmgntg ygtnytnytn     420
gargtncarg tnccngcngc nytngtncar ttyggncarw sngtnggnws ngtngtntay     480
gaytgyttyg argcngcnyt nggnwsngar gtnmgnatht ggwsntayac ncarccnmgn     540
taygaraarg arytnaayca yacncarcar ytnccngcny tnccntgggt naaygtnwsn     600
gcngayggng ayaaygtnca yytngtnytn aaygtnwsng argarcarca yttyggnytn     660
wsnytntayt ggaaycargt ncarggnccn ccnaarccnm gntggcayaa raayytnacn     720
ggnccncara thathacnyt naaycayacn gayytngtnc cntgyytntg yathcargtn     780
tggccnytng arccngayws ngtnmgnacn aayathtgyc cnttymgnga rgayccnmgn     840
gcncaycara ayytntggca rgcngcnmgn ytnmgnytny tnacnytnca rwsntggytn     900
ytngaygcnc cntgywsnyt nccngcngar gcngcnytnt gytggmgngc nccnggnggn     960
gayccntgyc arccnytngt nccnccnytn wsntgggara aygtnacngt ngayaargtn    1020
ytngarttyc nytnyytnaa rggncayccn aayytntgyg tncargtnaa ywsnwsngar    1080
aarytncary tncargartg yytntgggcn gaywsnytng gnccnytnaa rgaygaygtn    1140
ytnytnytng aracnmgngg nccncargay aaymgnwsny tntgygcnyt ngarccnwsn    1200
```

-continued

```
ggntgyacnw snytnccnws naargcnwsn acnmgngcng cnmgnytngg ngartayytn    1260
ytncargayy tncarwsngg ncartgyytn carytntggg aygaygayyt nggngcnytn    1320
tgggcntgyc cnatggayaa rtayathcay aarmgntggg cnytngtntg gytngcntgy    1380
ytnytnttyg cngcngcnyt nwsnytnath ytnytnytna araargayca ygcnaargcn    1440
gcngcnmgng gnmgngcngc nytnytnytn taywsngcng aygaywsngg nttygarmgn    1500
ytngtnggng cnytngcnws ngcnytntgy carytnccny tnmgngtngc ngtngay

```
Ile Gln Val Trp Pro Leu Glu Pro Asp Ser Val Arg Thr Asn Ile Cys
145                 150                 155                 160 ccc ttc agg gag gac ccc cgc gca cac cag aac ctc tgg caa gcc gcc      529
Pro Phe Arg Glu Asp Pro Arg Ala His Gln Asn Leu Trp Gln Ala Ala
                165                 170                 175 cga ctg cga ctg ctg acc ctg cag agc tgg ctg ctg gac gca ccg tgc      577
Arg Leu Arg Leu Leu Thr Leu Gln Ser Trp Leu Leu Asp Ala Pro Cys
            180                 185                 190 tcg ctg ccc gca gaa gcg gca ctg tgc tgg cgg gct ccg ggt ggg gac      625
Ser Leu Pro Ala Glu Ala Ala Leu Cys Trp Arg Ala Pro Gly Gly Asp
        195                 200                 205 ccc tgc cag cca ctg gtc cca ccg ctt tcc tgg gag aac gtc act gtg      673
Pro Cys Gln Pro Leu Val Pro Pro Leu Ser Trp Glu Asn Val Thr Val
    210                 215                 220 gac gtg aac agc tcg gag aag ctg cag ctg cag gag tgc ttg tgg gct      721
Asp Val Asn Ser Ser Glu Lys Leu Gln Leu Gln Glu Cys Leu Trp Ala
225                 230                 235                 240 gac tcc ctg ggg cct ctc aaa gac gat gtg cta ctg ttg gag aca cga      769
Asp Ser Leu Gly Pro Leu Lys Asp Asp Val Leu Leu Leu Glu Thr Arg
                245                 250                 255 ggc ccc cag gac aac aga tcc ctc tgt gcc ttg gaa ccc agt ggc tgt      817
Gly Pro Gln Asp Asn Arg Ser Leu Cys Ala Leu Glu Pro Ser Gly Cys
            260                 265                 270 act tca cta ccc agc aaa gcc tcc acg agg gca gct cgc ctt gga gag      865
Thr Ser Leu Pro Ser Lys Ala Ser Thr Arg Ala Ala Arg Leu Gly Glu
        275                 280                 285 tac tta cta caa gac ctg cag tca ggc agt gct ctg cag cta tgg gac      913
Tyr Leu Leu Gln Asp Leu Gln Ser Gly Gln Cys Leu Gln Leu Trp Asp
    290                 295                 300 gat gac ttg gga gcg cta tgg gcc tgc ccc atg gac aaa tac atc cac      961
Asp Asp Leu Gly Ala Leu Trp Ala Cys Pro Met Asp Lys Tyr Ile His
305                 310                 315                 320 aag cgc tgg gcc ctc gtg tgg ctg gcc tgc cta atc ttt gcc gct gcg     1009
Lys Arg Trp Ala Leu Val Trp Leu Ala Cys Leu Leu Phe Ala Ala Ala
                325                 330                 335 ctt tcc ctc atc ctc ctt ctc aaa aag gat cac gcg aaa ggg tgg ctg     1057
Leu Ser Leu Ile Leu Leu Leu Lys Lys Asp His Ala Lys Gly Trp Leu
            340                 345                 350 agg ctc ttg aaa cag gac gtc cgc tcg ggg gcg gcc gcc agg ggc cgc     1105
Arg Leu Leu Lys Gln Asp Val Arg Ser Gly Ala Ala Ala Arg Gly Arg
        355                 360                 365 gcg gct ctg ctc ctc tac tca gcc gat gac tcg ggt ttc gag cgc ctg     1153
Ala Ala Leu Leu Leu Tyr Ser Ala Asp Asp Ser Gly Phe Glu Arg Leu
    370                 375                 380 gtg ggc gcc ctg gcg tcg gcc ctg tgc cag ctg ccg ctg cgc gtg gcc     1201
Val Gly Ala Leu Ala Ser Ala Leu Cys Gln Leu Pro Leu Arg Val Ala
385                 390                 395                 400 gta gac ctg tgg agc cgt cgt gaa ctg agc gcg cag ggg ccc gtg gct     1249
Val Asp Leu Trp Ser Arg Arg Glu Leu Ser Ala Gln Gly Pro Val Ala
                405                 410                 415 tgg ttt cac gcg cag cgg cgc cag acc ctg cag gag ggc ggc gtg gtg     1297
Trp Phe His Ala Gln Arg Arg Gln Thr Leu Gln Glu Gly Gly Val Val
            420                 425                 430 gtc ttg ctc ttc tct ccc ggt gcg gtg gcg ctg tgc agc gag tgg cta     1345
Val Leu Leu Phe Ser Pro Gly Ala Val Ala Leu Cys Ser Glu Trp Leu
        435                 440                 445 cag gat ggg gtg tcc ggg ccc ggg gcg cac ggc ccg cac gac gcc ttc     1393
Gln Asp Gly Val Ser Gly Pro Gly Ala His Gly Pro His Asp Ala Phe
    450                 455                 460
```

-continued

```
cgc gcc tcg ctc agc tgc gtg ctg ccc gac ttc ttg cag ggc cgg gcg      1441
Arg Ala Ser Leu Ser Cys Val Leu Pro Asp Phe Leu Gln Gly Arg Ala
465                 470                 475                 480 ccc ggc agc tac gtg ggg gcc tgc ttc gac agg ctg ctc cac ccg gac      1489
Pro Gly Ser Tyr Val Gly Ala Cys Phe Asp Arg Leu Leu His Pro Asp
                485                 490                 495 gcc gta ccc gcc ctt ttc cgc acc gtg ccc gtc ttc aca ctg ccc tcc      1537
Ala Val Pro Ala Leu Phe Arg Thr Val Pro Val Phe Thr Leu Pro Ser
            500                 505                 510 caa ctg cca gac ttc ctg ggg gcc ctg cag cag cct cgc gcc ccg cgt      1585
Gln Leu Pro Asp Phe Leu Gly Ala Leu Gln Gln Pro Arg Ala Pro Arg
        515                 520                 525 tcc ggg cgg ctc caa gag aga gcg gag caa gtg tcc cgg gcc ctt cag      1633
Ser Gly Arg Leu Gln Glu Arg Ala Glu Gln Val Ser Arg Ala Leu Gln
530                 535                 540 cca gcc ctg gat agc tac ttc cat ccc ccg ggg act ccc gcg ccg gga      1681
Pro Ala Leu Asp Ser Tyr Phe His Pro Pro Gly Thr Pro Ala Pro Gly
545                 550                 555                 560 cgc ggg gtg gga cca ggg gcg gga cct ggg gcg ggg gac ggg act          1726
Arg Gly Val Gly Pro Gly Ala Gly Pro Gly Ala Gly Asp Gly Thr
                565                 570                 575 taaataaagg cagacgctgt ttttcta                                        1753
```

```
<210> SEQ ID NO 5
<211> LENGTH: 575
<212> TYPE: PRT
<213> ORGANISM: Homo sapiens

<400> SEQUENCE: 5

Glu Glu Pro Arg Asn Ala Ser Leu Gln Ala Gln Val Val Leu Ser Phe
1               5                   10                  15

Gln Ala Tyr Pro Thr Ala Arg Cys Val Leu Glu Val Gln Val Pro
            20                  25                  30

Ala Ala Leu Val Gln Phe Gly Gln Ser Val Gly Ser Val Val Tyr Asp
        35                  40                  45

Cys Phe Glu Ala Ala Leu Gly Ser Glu Val Arg Ile Trp Ser Tyr Thr
    50                  55                  60

Gln Pro Arg Tyr Glu Lys Glu Leu Asn His Thr Gln Gln Leu Pro Ala
65                  70                  75                  80

Leu Pro Trp Leu Asn Val Ser Ala Asp Gly Asp Asn Val His Leu Val
                85                  90                  95

Leu Asn Val Ser Glu Glu Gln His Phe Gly Leu Ser Leu Tyr Trp Asn
            100                 105                 110

Gln Val Gln Gly Pro Pro Lys Pro Arg Trp His Lys Asn Leu Thr Gly
        115                 120                 125

Pro Gln Ile Ile Thr Leu Asn His Thr Asp Leu Val Pro Cys Leu Cys
    130                 135                 140

Ile Gln Val Trp Pro Leu Glu Pro Asp Ser Val Arg Thr Asn Ile Cys
145                 150                 155                 160

Pro Phe Arg Glu Asp Pro Arg Ala His Gln Asn Leu Trp Gln Ala Ala
                165                 170                 175

Arg Leu Arg Leu Leu Thr Leu Gln Ser Trp Leu Leu Asp Ala Pro Cys
            180                 185                 190

Ser Leu Pro Ala Glu Ala Ala Leu Cys Trp Arg Ala Pro Gly Gly Asp
        195                 200                 205

Pro Cys Gln Pro Leu Val Pro Pro Leu Ser Trp Glu Asn Val Thr Val
    210                 215                 220
```

```
Asp Val Asn Ser Ser Glu Lys Leu Gln Leu Gln Glu Cys Leu Trp Ala
225                 230                 235                 240

Asp Ser Leu Gly Pro Leu Lys Asp Val Leu Leu Leu Glu Thr Arg
            245                 250                 255

Gly Pro Gln Asp Asn Arg Ser Leu Cys Ala Leu Glu Pro Ser Gly Cys
            260                 265                 270

Thr Ser Leu Pro Ser Lys Ala Ser Thr Arg Ala Ala Arg Leu Gly Glu
            275                 280                 285

Tyr Leu Leu Gln Asp Leu Gln Ser Gly Gln Cys Leu Gln Leu Trp Asp
    290                 295                 300

Asp Asp Leu Gly Ala Leu Trp Ala Cys Pro Met Asp Lys Tyr Ile His
305                 310                 315                 320

Lys Arg Trp Ala Leu Val Trp Leu Ala Cys Leu Leu Phe Ala Ala Ala
                325                 330                 335

Leu Ser Leu Ile Leu Leu Leu Lys Lys Asp His Ala Lys Gly Trp Leu
            340                 345                 350

Arg Leu Leu Lys Gln Asp Val Arg Ser Gly Ala Ala Ala Arg Gly Arg
            355                 360                 365

Ala Ala Leu Leu Leu Tyr Ser Ala Asp Asp Ser Gly Phe Glu Arg Leu
370                 375                 380

Val Gly Ala Leu Ala Ser Ala Leu Cys Gln Leu Pro Leu Arg Val Ala
385                 390                 395                 400

Val Asp Leu Trp Ser Arg Arg Glu Leu Ser Ala Gln Gly Pro Val Ala
                405                 410                 415

Trp Phe His Ala Gln Arg Arg Gln Thr Leu Gln Glu Gly Gly Val Val
            420                 425                 430

Val Leu Leu Phe Ser Pro Gly Ala Val Ala Leu Cys Ser Glu Trp Leu
            435                 440                 445

Gln Asp Gly Val Ser Gly Pro Gly Ala His Gly Pro His Asp Ala Phe
    450                 455                 460

Arg Ala Ser Leu Ser Cys Val Leu Pro Asp Phe Leu Gln Gly Arg Ala
465                 470                 475                 480

Pro Gly Ser Tyr Val Gly Ala Cys Phe Asp Arg Leu Leu His Pro Asp
                485                 490                 495

Ala Val Pro Ala Leu Phe Arg Thr Val Pro Val Phe Thr Leu Pro Ser
            500                 505                 510

Gln Leu Pro Asp Phe Leu Gly Ala Leu Gln Gln Pro Arg Ala Pro Arg
            515                 520                 525

Ser Gly Arg Leu Gln Glu Arg Ala Glu Gln Val Ser Arg Ala Leu Gln
    530                 535                 540

Pro Ala Leu Asp Ser Tyr Phe His Pro Pro Gly Thr Pro Ala Pro Gly
545                 550                 555                 560

Arg Gly Val Gly Pro Gly Ala Gly Pro Gly Ala Gly Asp Gly Thr
                565                 570                 575

<210> SEQ ID NO 6
<211> LENGTH: 1725
<212> TYPE: DNA
<213> ORGANISM: Artificial Sequence
<220> FEATURE:
<223> OTHER INFORMATION: This degenerate sequence encodes the amino acid
      sequence of SEQ ID NO:5.
<220> FEATURE:
<221> NAME/KEY: variation
<222> LOCATION: (1)...(1725)
<223> OTHER INFORMATION: N is any nucleotide.
```

-continued

<220> FEATURE:
<221> NAME/KEY: misc_feature
<222> LOCATION: (1)...(1725)
<223> OTHER INFORMATION: n = A,T,C or G

<400> SEQUENCE: 6

```
gargarccnm gnaaygcnws nytncargcn cargtngtny tnwsnttyca rgcntayccn     60
acngcnmgnt gygtnytnyt ngargtncar gtnccngcng cnytngtnca rttyggncar    120
wsngtnggnw sngtngtnta ygaytgytty gargcngcny tnggnwsnga rgtnmgnath    180
tggwsntaya cncarccnmg ntaygaraar garytnaayc ayacncarca rytnccngcn    240
ytnccntggy tnaaygtnws ngcngayggn gayaaygtnc ayytngtnyt naaygtnwsn    300
gargarcarc ayttyggnyt nwsnytntay tggaaycarg tncarggncc nccnaarccn    360
mgntggcaya araayytnac nggnccncar athathacny tnaaycayac ngayytngtn    420
ccntgyytnt gyathcargt ntggccnytn garccngayw sngtnmgnac naayathtgy    480
ccnttymgng argayccnmg ngcncaycar aayytntggc argcngcnmg nytnmgnytn    540
ytnacnytnc arwsntggyt nytngaygcn ccntgywsny tnccngcnga rgcngcnytn    600
tgytggmgng cnccnggngg ngayccntgy carccnytng tnccnccnyt nwsntgggar    660
aaygtnacng tngaygtnaa ywsnwsngar aarytncary tncargartg yytntgggcn    720
gaywsnytng gnccnytnaa rgaygaygtn ytnytnytng aracnmgngg nccncargay    780
aaymgnwsny tntgygcnyt ngarccnwsn ggntgyacnw snytnccnws naargcnwsn    840
acnmgngcng cnmgnytngg ngartayytn ytncargayy tncarwsngg ncartgyytn    900
carytntggg aygaygayyt nggngcnytn tgggcntgyc cnatggayaa rtayathcay    960
aarmgntggg cnytngtntg gytngcntgy ytnytnttyg cngcngcnyt nwsnytnath   1020
ytnytnytna araargayca ygcnaarggn tggytnmgny tnytnaarca rgaygtnmgn   1080
wsnggngcng cngcnmgngg nmgngcngcn ytnytnytnt aywsngcnga ygaywsnggn   1140
ttygarmgny tngtnggngc nytngcnwsn gcnytntgyc arytnccnyt nmgngtngcn   1200
gtngayytnt ggwsnmgnmg ngarytnwsn gcncarggnc cngtngcntg gttycaygcn   1260
carmgnmgnc aracnytnca rgarggnggn gtngtngtny tnytnttyws nccnggngcn   1320
gtngcnytnt gywsngartg gytncargay ggngtnwsng gnccnggngc ncayggnccn   1380
caygaygcnt tymgngcnws nytnwsntgy gtnytnccng ayttyytnca rggnmgngcn   1440
ccnggnwsnt aygtnggngc ntgyttygay mgnytnytnc ayccngaygc ngtnccngcn   1500
ytnttymgna cngtnccngt nttyacnytn ccnwsncary tnccngaytt yytnggngcn   1560
ytncarcarc cnmgngcncc nmgnwsnggn mgnytncarg armgngcnga rcargtnwsn   1620
mgngcnytnc arccngcnyt ngaywsntay ttycayccnc cnggnacncc ngcnccnggn   1680
mgnggngtng gnccnggngc nggnccnggn gcnggngayg gnacn                   1725
```

<210> SEQ ID NO 7
<211> LENGTH: 16
<212> TYPE: PRT
<213> ORGANISM: Artificial Sequence
<220> FEATURE:
<223> OTHER INFORMATION: Peptide linker.

<400> SEQUENCE: 7

```
Gly Gly Ser Gly Gly Ser Gly Gly Gly Gly Ser Gly Gly Gly Gly Ser
 1               5                  10                  15

-continued

```
<210> SEQ ID NO 8
<211> LENGTH: 21
<212> TYPE: DNA
<213> ORGANISM: Artificial Sequence
<220> FEATURE:
<223> OTHER INFORMATION: PCR primer

<400> SEQUENCE: 8
cggcgtggtg gtcttgctct t                                             21

<210> SEQ ID NO 9
<211> LENGTH: 21
<212> TYPE: DNA
<213> ORGANISM: Artificial Sequence
<220> FEATURE:
<223> OTHER INFORMATION: PCR primer.

<400> SEQUENCE: 9
tcccgtcccc cgccccaggt c                                             21

<210> SEQ ID NO 10
<211> LENGTH: 688
<212> TYPE: PRT
<213> ORGANISM: Artificial Sequence
<220> FEATURE:
<223> OTHER INFORMATION: Chimeric Zcytor14 protein.

<400> SEQUENCE: 10
```

Met Pro Val Pro Trp Phe Leu Leu Ser Leu Ala Leu Gly Arg Ser Pro
 1               5                  10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Ala Leu Pro Trp Leu Asn Val Ser Ala Asp Gly Asp Asn Val His Leu
        195                 200                 205

Val Leu Asn Val Ser Glu Glu Gln His Phe Gly Leu Ser Leu Tyr Trp
    210                 215                 220

Asn Gln Val Gln Gly Pro Pro Lys Pro Arg Trp His Lys Asn Leu Thr
225                 230                 235                 240

Gly Pro Gln Ile Ile Thr Leu Asn His Thr Asp Leu Val Pro Cys Leu

-continued

```
                245                 250                 255
Cys Ile Gln Val Trp Pro Leu Glu Pro Asp Ser Val Arg Thr Asn Ile
                    260                 265                 270
Cys Pro Phe Arg Glu Asp Pro Arg Ala His Gln Asn Leu Trp Gln Ala
                275                 280                 285
Ala Arg Leu Arg Leu Leu Thr Leu Gln Ser Trp Leu Leu Asp Ala Pro
            290                 295                 300
Cys Ser Leu Pro Ala Glu Ala Ala Leu Cys Trp Arg Ala Pro Gly Gly
305                 310                 315                 320
Asp Pro Cys Gln Pro Leu Val Pro Pro Leu Ser Trp Glu Asn Val Thr
                325                 330                 335
Val Asp Val Asn Ser Ser Glu Lys Leu Gln Leu Gln Glu Cys Leu Trp
                340                 345                 350
Ala Asp Ser Leu Gly Pro Leu Lys Asp Asp Val Leu Leu Leu Glu Thr
            355                 360                 365
Arg Gly Pro Gln Asp Asn Arg Ser Leu Cys Ala Leu Glu Pro Ser Gly
        370                 375                 380
Cys Thr Ser Leu Pro Ser Lys Ala Ser Thr Arg Ala Ala Arg Leu Gly
385                 390                 395                 400
Glu Tyr Leu Leu Gln Asp Leu Gln Ser Gly Gln Cys Leu Gln Leu Trp
                405                 410                 415
Asp Asp Asp Leu Gly Ala Leu Trp Ala Cys Pro Met Asp Lys Tyr Ile
                420                 425                 430
His Lys Arg Trp Ala Leu Val Trp Leu Ala Cys Leu Leu Phe Ala Ala
            435                 440                 445
Ala Leu Ser Leu Ile Leu Leu Lys Lys Asp His Ala Lys Gly Trp
450                 455                 460
Leu Arg Leu Leu Lys Gln Asp Val Arg Ser Gly Ala Ala Ala Arg Gly
465                 470                 475                 480
Arg Ala Ala Leu Leu Leu Tyr Ser Ala Asp Asp Ser Gly Phe Glu Arg
                485                 490                 495
Leu Val Gly Ala Leu Ala Ser Ala Leu Cys Gln Leu Pro Leu Arg Val
                500                 505                 510
Ala Val Asp Leu Trp Ser Arg Arg Glu Leu Ser Ala Gln Gly Pro Val
            515                 520                 525
Ala Trp Phe His Ala Gln Arg Arg Gln Thr Leu Gln Glu Gly Gly Val
            530                 535                 540
Val Val Leu Leu Phe Ser Pro Gly Ala Val Ala Leu Cys Ser Glu Trp
545                 550                 555                 560
Leu Gln Asp Gly Val Ser Gly Pro Gly Ala His Gly Pro His Asp Ala
                565                 570                 575
Phe Arg Ala Ser Leu Ser Cys Val Leu Pro Asp Phe Leu Gln Gly Arg
            580                 585                 590
Ala Pro Gly Ser Tyr Val Gly Ala Cys Phe Asp Arg Leu Leu His Pro
        595                 600                 605
Asp Ala Val Pro Ala Leu Phe Arg Thr Val Pro Val Phe Thr Leu Pro
    610                 615                 620
Ser Gln Leu Pro Asp Phe Leu Gly Ala Leu Gln Gln Pro Arg Ala Pro
625                 630                 635                 640
Arg Ser Gly Arg Leu Gln Glu Arg Ala Glu Gln Val Ser Arg Ala Leu
                645                 650                 655
Gln Pro Ala Leu Asp Ser Tyr Phe His Pro Gly Thr Pro Ala Pro
            660                 665                 670
```

```
Gly Arg Gly Val Gly Pro Gly Ala Gly Pro Gly Ala Gly Asp Gly Thr
            675                 680                 685

<210> SEQ ID NO 11
<211> LENGTH: 705
<212> TYPE: PRT
<213> ORGANISM: Artificial Sequence
<220> FEATURE:
<223> OTHER INFORMATION: Chimeric Zcytor14 protein.

<400> SEQUENCE: 11

Met Pro Val Pro Trp Phe Leu Leu Ser Leu Ala Leu Gly Arg Ser Pro
  1               5                  10                  15

Val Val Leu Ser Leu Glu Arg Leu Val Gly Pro Gln Asp Ala Thr His
             20                  25                  30

Cys Ser Pro Gly Leu Ser Cys Arg Leu Trp Asp Ser Asp Ile Leu Cys
         35                  40                  45

Leu Pro Gly Asp Ile Val Pro Ala Pro Gly Pro Val Leu Ala Pro Thr
 50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                 85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Ala Leu Pro Trp Leu Asn Val Ser Ala Asp Gly Asp Asn Val His Leu
        195                 200                 205

Val Leu Asn Val Ser Glu Glu Gln His Phe Gly Leu Ser Leu Tyr Trp
210                 215                 220

Asn Gln Val Gln Gly Pro Pro Lys Pro Arg Trp His Lys Asn Leu Thr
225                 230                 235                 240

Gly Pro Gln Ile Ile Thr Leu Asn His Thr Asp Leu Val Pro Cys Leu
                245                 250                 255

Cys Ile Gln Val Trp Pro Leu Glu Pro Asp Ser Val Arg Thr Asn Ile
            260                 265                 270

Cys Pro Phe Arg Glu Asp Pro Arg Ala His Gln Asn Leu Trp Gln Ala
        275                 280                 285

Ala Arg Leu Arg Leu Leu Thr Leu Gln Ser Trp Leu Leu Asp Ala Pro
290                 295                 300

Cys Ser Leu Pro Ala Glu Ala Ala Leu Cys Trp Arg Ala Pro Gly Gly
305                 310                 315                 320

Asp Pro Cys Gln Pro Leu Val Pro Pro Leu Ser Trp Glu Asn Val Thr
                325                 330                 335

Val Asp Lys Val Leu Glu Phe Pro Leu Leu Lys Gly His Pro Asn Leu
            340                 345                 350
```

```
Cys Val Gln Val Asn Ser Ser Glu Lys Leu Gln Leu Gln Glu Cys Leu
            355                 360                 365
Trp Ala Asp Ser Leu Gly Pro Leu Lys Asp Asp Val Leu Leu Leu Glu
        370                 375                 380
Thr Arg Gly Pro Gln Asp Asn Arg Ser Leu Cys Ala Leu Glu Pro Ser
385                 390                 395                 400
Gly Cys Thr Ser Leu Pro Ser Lys Ala Ser Thr Arg Ala Ala Arg Leu
                405                 410                 415
Gly Glu Tyr Leu Leu Gln Asp Leu Gln Ser Gly Gln Cys Leu Gln Leu
            420                 425                 430
Trp Asp Asp Leu Gly Ala Leu Trp Ala Cys Pro Met Asp Lys Tyr
        435                 440                 445
Ile His Lys Arg Trp Ala Leu Val Trp Leu Ala Cys Leu Leu Phe Ala
        450                 455                 460
Ala Ala Leu Ser Leu Ile Leu Leu Leu Lys Lys Asp His Ala Lys Gly
465                 470                 475                 480
Trp Leu Arg Leu Leu Lys Gln Asp Val Arg Ser Gly Ala Ala Ala Arg
                485                 490                 495
Gly Arg Ala Ala Leu Leu Leu Tyr Ser Ala Asp Asp Ser Gly Phe Glu
            500                 505                 510
Arg Leu Val Gly Ala Leu Ala Ser Ala Leu Cys Gln Leu Pro Leu Arg
        515                 520                 525
Val Ala Val Asp Leu Trp Ser Arg Arg Glu Leu Ser Ala Gln Gly Pro
    530                 535                 540
Val Ala Trp Phe His Ala Gln Arg Arg Gln Thr Leu Gln Glu Gly Gly
545                 550                 555                 560
Val Val Val Leu Leu Phe Ser Pro Gly Ala Val Ala Leu Cys Ser Glu
                565                 570                 575
Trp Leu Gln Asp Gly Val Ser Gly Pro Gly Ala His Gly Pro His Asp
            580                 585                 590
Ala Phe Arg Ala Ser Leu Ser Cys Val Leu Pro Asp Phe Leu Gln Gly
        595                 600                 605
Arg Ala Pro Gly Ser Tyr Val Gly Ala Cys Phe Asp Arg Leu Leu His
        610                 615                 620
Pro Asp Ala Val Pro Ala Leu Phe Arg Thr Val Pro Val Phe Thr Leu
625                 630                 635                 640
Pro Ser Gln Leu Pro Asp Phe Leu Gly Ala Leu Gln Gln Pro Arg Ala
                645                 650                 655
Pro Arg Ser Gly Arg Leu Gln Glu Arg Ala Glu Gln Val Ser Arg Ala
            660                 665                 670
Leu Gln Pro Ala Leu Asp Ser Tyr Phe His Pro Pro Gly Thr Pro Ala
        675                 680                 685
Pro Gly Arg Gly Val Gly Pro Gly Ala Gly Pro Gly Ala Gly Asp Gly
        690                 695                 700
Thr
705

<210> SEQ ID NO 12
<211> LENGTH: 675
<212> TYPE: PRT
<213> ORGANISM: Artificial Sequence
<220> FEATURE:
<223> OTHER INFORMATION: Chimeric Zcytor14 protein.

<400> SEQUENCE: 12
```

-continued

```
Met Pro Val Pro Trp Phe Leu Leu Ser Leu Ala Leu Gly Arg Ser Pro
 1               5                  10                  15

Val Val Leu Ser Leu Glu Arg Leu Val Gly Pro Gln Asp Ala Thr His
                20                  25                  30

Cys Ser Pro Gly Leu Ser Cys Arg Leu Trp Asp Ser Asp Ile Leu Cys
            35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
    115                 120                 125

Phe Gln Ala Tyr Pro Thr Ala Arg Cys Val Leu Leu Glu Val Gln Val
130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Ala Leu Pro Trp Leu Asn Val Ser Ala Asp Gly Asp Asn Val His Leu
    195                 200                 205

Val Leu Asn Val Ser Glu Glu Gln His Phe Gly Leu Ser Leu Tyr Trp
210                 215                 220

Asn Gln Val Gln Gly Pro Pro Lys Pro Arg Trp His Lys Asn Leu Thr
225                 230                 235                 240

Gly Pro Gln Ile Ile Thr Leu Asn His Thr Asp Leu Val Pro Cys Leu
                245                 250                 255

Cys Ile Gln Val Trp Pro Leu Glu Pro Asp Ser Val Arg Thr Asn Ile
            260                 265                 270

Cys Pro Phe Arg Glu Asp Pro Arg Ala His Gln Asn Leu Trp Gln Ala
    275                 280                 285

Ala Arg Leu Arg Leu Leu Thr Leu Gln Ser Trp Leu Leu Asp Ala Pro
290                 295                 300

Cys Ser Leu Pro Ala Glu Ala Ala Leu Cys Trp Arg Ala Pro Gly Gly
305                 310                 315                 320

Asp Pro Cys Gln Pro Leu Val Pro Pro Leu Ser Trp Glu Asn Val Thr
                325                 330                 335

Val Asp Val Asn Ser Ser Glu Lys Leu Gln Leu Gln Glu Cys Leu Trp
            340                 345                 350

Ala Asp Ser Leu Gly Pro Leu Lys Asp Asp Val Leu Leu Leu Glu Thr
    355                 360                 365

Arg Gly Pro Gln Asp Asn Arg Ser Leu Cys Ala Leu Glu Pro Ser Gly
370                 375                 380

Cys Thr Ser Leu Pro Ser Lys Ala Ser Thr Arg Ala Ala Arg Leu Gly
385                 390                 395                 400

Glu Tyr Leu Leu Gln Asp Leu Gln Ser Gly Gln Cys Leu Gln Leu Trp
                405                 410                 415
```

-continued

```
Asp Asp Asp Leu Gly Ala Leu Trp Ala Cys Pro Met Asp Lys Tyr Ile
            420                 425                 430

His Lys Arg Trp Ala Leu Val Trp Leu Ala Cys Leu Leu Phe Ala Ala
        435                 440                 445

Ala Leu Ser Leu Ile Leu Leu Leu Lys Lys Asp His Ala Lys Ala Ala
    450                 455                 460

Ala Arg Gly Arg Ala Ala Leu Leu Leu Tyr Ser Ala Asp Asp Ser Gly
465             470                 475                 480

Phe Glu Arg Leu Val Gly Ala Leu Ala Ser Ala Leu Cys Gln Leu Pro
            485                 490                 495

Leu Arg Val Ala Val Asp Leu Trp Ser Arg Arg Glu Leu Ser Ala Gln
            500                 505                 510

Gly Pro Val Ala Trp Phe His Ala Gln Arg Arg Gln Thr Leu Gln Glu
            515                 520                 525

Gly Gly Val Val Val Leu Leu Phe Ser Pro Gly Ala Val Ala Leu Cys
    530                 535                 540

Ser Glu Trp Leu Gln Asp Gly Val Ser Gly Pro Gly Ala His Gly Pro
545             550                 555                 560

His Asp Ala Phe Arg Ala Ser Leu Ser Cys Val Leu Pro Asp Phe Leu
            565                 570                 575

Gln Gly Arg Ala Pro Gly Ser Tyr Val Gly Ala Cys Phe Asp Arg Leu
            580                 585                 590

Leu His Pro Asp Ala Val Pro Ala Leu Phe Arg Thr Val Pro Val Phe
        595                 600                 605

Thr Leu Pro Ser Gln Leu Pro Asp Phe Leu Gly Ala Leu Gln Gln Pro
    610                 615                 620

Arg Ala Pro Arg Ser Gly Arg Leu Gln Glu Arg Ala Glu Gln Val Ser
625             630                 635                 640

Arg Ala Leu Gln Pro Ala Leu Asp Ser Tyr Phe His Pro Pro Gly Thr
            645                 650                 655

Pro Ala Pro Gly Arg Gly Val Gly Pro Gly Ala Gly Pro Gly Ala Gly
            660                 665                 670

Asp Gly Thr
        675
```

INTERLEUKIN-17 RECEPTOR HOMOLOGUE

CROSS-REFERENCE TO RELATED APPLICATIONS

This application is a continuation of U.S. application Ser. No. 10/458,647, filed Jun. 10, 2003 now abandoned, which is a continuation of U.S. application Ser. No. 09/608,918, filed Jun. 30, 2000 now abandoned, which claims the benefit of U.S. Provisional Application Ser. No. 60/142,555, filed Jul. 7, 1999, both of which are herein incorporated by reference.

TECHNICAL FIELD

The present invention relates generally to a new protein expressed by human cells. In particular, the present invention relates to a novel gene that encodes a receptor, designated as "Zcytor14," and to nucleic acid molecules encoding Zcytor14 polypeptides.

BACKGROUND OF THE INVENTION

Cytokines are soluble, small proteins that mediate a variety of biological effects, including the regulation of the growth and differentiation of many cell types (see, for example, Arai et al., *Ann. Rev. Biochem.* 59:783 (1990); Mosmann, *Curr. Opin. Immunol.* 3:311 (1991); Paul and Seder, *Cell* 76:241 (1994)). Proteins that constitute the cytokine group include interleukins, interferons, colony stimulating factors, tumor necrosis factors, and other regulatory molecules. For example, human interleukin-17 is a cytokine that stimulates the expression of interleukin-6, intracellular adhesion molecule 1, interleukin-8, granulocyte macrophage colony-stimulating factor, and prostaglandin E2 expression, and plays a role in the preferential maturation of CD34+ hematopoietic precursors into neutrophils (Yao et al., *J Immunol.* 155:5483 (1995); Fossiez et al., *J. Exp. Med.* 183:2593 (1996)).

Receptors that bind cytokines are typically composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains. For example, the receptor chains responsible for binding and/or transducing the effect of interferons are members of the type II cytokine receptor family, based upon a characteristic 200 residue extracellular domain.

The demonstrated in vivo activities of cytokines and their receptors illustrate the clinical potential of, and need for, other cytokines, cytokine receptors, cytokine agonists, and cytokine antagonists.

SUMMARY OF THE INVENTION

The present invention provides a novel receptor, designated "Zcytor14." The present invention also provides Zcytor14 polypeptides and Zcytor14 fusion proteins, as well as nucleic acid molecules encoding such polypeptides and proteins, and methods for using these nucleic acid molecules and amino acid sequences.

DETAILED DESCRIPTION OF THE INVENTION

1. Overview

An illustrative nucleotide sequence that encodes Zcytor14 is provided by SEQ ID NO: 1. The encoded polypeptide has the following amino acid sequence: MPVPWFLLSL ALGR-SPVVLS LERLVGPQDA THCSPGLSCR LWDSDILCLP GDIVPAPGPV LAPTHLQTEL VLRCQKETDC DLCLR-VAVHL AVHGHWEEPE DEEKFGGAAD SGVEEPRNAS LQAQVVLSFQ AYPTARCVLL EVQVPAALVQ FGQS-VGSVVY DCFEAALGSE VRIWSYTQPR YEKEL-NHTQQ LPALPWLNVS ADGDNVHLVL NVSEEQHFGL SLYWNQVQGP PKPRWHKNLT GPQIITLNHT DLVP-CLCIQV WPLEPDSVRT NICPFREDPR AHQNLWQAAR LRLLTLQSWL LDAPCSLPAE AALCWRAPGG DPCQ-PLVPPL SWENVTVDKV LEFPLLKGHP NLCVQVNSSE KLQLQECLWA DSLGPLKDDV LLLETRGPQD NRSL-CALEPS GCTSLPSKAS TRAARLGEYL LQDLQSGQCL QLWDDDLGAL WACPMDKYIH KRWALVWLAC LLFAAALSLI LLLKKDHAKA AARGRAALLL YSADDSGFER LVGALASALC QLPLRVAVDL WSR-RELSAQG PVAWFHAQRR QTLQEGGVVV LLFSP-GAVAL CSEWLQDGVS GPGAHGPHDA FRASLSCVLP DFLQGRAPGS YVGACFDRLL HPDAVPALFR TVPVFTLPSQ LPDFLGALQQ PRAPRSGRLQ ERAEQVSRAL QPALDSYFHP PGTPAPGRGV GPGAG-PGAGD GT (SEQ ID NO:2).

Thus, the Zcytor14 gene encodes a polypeptide of 692 amino acids. Features of Zcytor14 include a putative signal sequence (amino acid residues 1 to 20 of SEQ ID NO:2), an extracellular domain (amino acid residues 21 to 452 of SEQ ID NO:2), a transmembrane domain (amino acid residues 453 to 473 of SEQ ID NO:2), and an intracellular domain (comprising amino acid residues 474 to 677 of SEQ ID NO:2).

A variant Zcytor14 protein, designated as "Zcytor14-1," was identified, which has the following amino acid sequence: EEPRNASLQA QVVLSFQAYP TARCVLLEVQ VPAALVQFGQ SVGSVVYDCF EAALGSEVRI WSYTQPRYEK ELNHTQQLPA LPWLNVSADG DNVHLVLNVS EEQHFGLSLY WNQVQGPPKP RWH-KNLTGPQ IITLNHTDLV PCLCIQVWPL EPDSVRTNIC PFREDPRAHQ NLWQAARLRL LTLQSWLLDA PCS-LPAEAAL CWRAPGGDPC QPLVPPLSWE NVTVD-VNSSE KLQLQECLWA DSLGPLKDDV LLLETRGPQD NRSLCALEPS GCTSLPSKAS TRAARLGEYL LQDLQS-GQCL QLWDDDLGAL WACPMDKYIH KRWALVW-LAC LLFAAALSLI LLLKKDHAKG WLRLLKQDVR SGAAARGRAA LLLYSADDSG FERLVGALAS ALCQL-PLRVA VDLWSRRELS AQGPVAWFHA QRRQTLQEGG VVVLLFSPGA VALCSEWLQD GVSGPGAHGP HDAFRASLSC VLPDFLQGRA PGSYVGACFD RLLHP-DAVPA LFRTVPVFTL PSQLPDFLGA LQQPRAPRSG RLQERAEQVS RALQPALDSY FHPPGTPAPG RGVGP-GAGPG AGDGT (SEQ ID NO:5). An illustrative nucleotide sequence that encodes this polypeptide is provided by SEQ ID NO:4.

Sequence analysis revealed that Zcytor14-1 is a truncated form of receptor polypeptide. That is, Zcytor14-1 lacks amino acid residues 1-113 of SEQ ID NO:2. SEQ ID NO:10 presents an amino acid sequence of a Zcytor14-1 polypeptide that includes the N-terminal portion of Zcytor14.

A comparison of the Zcytor14 and Zcytor14-1 amino acid sequences also indicated that the two polypeptides represent alternatively spliced variants. The amino acid sequence of Zcytor14 includes a 17 amino acid segment (amino acid residues 339 to 355 of SEQ ID NO:2), which Zcytor14-1 lacks, while Zcytor14 lacks, following amino acid 479, a 13 amino acid segment found in Zcytor14-1 (amino acid residues 350 to 362 of SEQ ID NO:5). A polypeptide that contains both amino acid segments is provided by SEQ ID NO:11, whereas SEQ ID NO:12 presents the amino acid sequence of a polypeptide that lacks both 13 and 17 amino acid segments.

The Zcytor14 gene resides in chromosome 3p25-3p24. As discussed below, this region is associated with various disorders and diseases.

Northern analyses indicate that there is strong expression of the Zcytor14 gene in thyroid, adrenal gland, prostate, and liver tissues, and less expression in heart, small intestine, stomach, and trachea tissues. In contrast, there is little or no expression in brain, placenta, lung, skeletal muscle, kidney, pancreas, spleen, thymus, testis, ovary, colon, peripheral blood leukocytes, spinal cord, lymph node, and bone marrow. These observations show that Zcytor14 sequences can be used differentiate between various tissues.

As described below, the present invention provides isolated polypeptides comprising an amino acid sequence that is at least 70%, at least 80%, or at least 90% identical to a reference amino acid sequence selected from the group consisting of: (a) amino acid residues 21 to 452 of SEQ ID NO:2, (b) amino acid residues 21 to 435 of SEQ ID NO:10, (c) amino acid residues 21 to 677 of SEQ ID NO:2, and (d) amino acid residues 1 to 692 of SEQ ID NO:2, wherein the isolated polypeptide specifically binds with an antibody that specifically binds with a polypeptide consisting of either the amino acid sequence of SEQ ID NO:2, or the amino acid sequence of SEQ ID NO:10. Illustrative polypeptides include a polypeptide comprising the amino acid sequence of SEQ ID NO:2, SEQ ID NO:10, SEQ ID NO:11, or SEQ ID NO:12.

The present invention also provides isolated polypeptides comprising an extracellular domain, wherein the extracellular domain comprises either amino acid residues 21 to 452 of the amino acid sequence of SEQ ID NO:2 or amino acid residues 21 to 435 of the amino acid sequence of SEQ ID NO:10. Such polypeptides may further comprise a transmembrane domain that resides in a carboxyl-terminal position relative to the extracellular domain, wherein the transmembrane domain comprises amino acid residues 453 to 473 of SEQ ID NO:2. These polypeptides may also comprise an intracellular domain that resides in a carboxyl-terminal position relative to the transmembrane domain, wherein the intracellular domain comprises either amino acid residues 474 to 677 of SEQ ID NO:2, or amino acid residues 457 to 673 of SEQ ID NO:10, and optionally, a signal secretory sequence that resides in an amino-terminal position relative to the extracellular domain, wherein the signal secretory sequence comprises amino acid residues 1 to 20 of the amino acid sequence of SEQ ID NO:2.

The present invention also includes variant Zcytor14 polypeptides, wherein the amino acid sequence of the variant polypeptide shares an identity with the amino acid sequence of SEQ ID NO:2 selected from the group consisting of at least 70% identity, at least 80% identity, at least 90% identity, at least 95% identity, or greater than 95% identity, and wherein any difference between the amino acid sequence of the variant polypeptide and the amino acid sequence of SEQ ID NO:2 is due to one or more conservative amino acid substitutions.

The present invention further provides antibodies and antibody fragments that specifically bind with such polypeptides. Exemplary antibodies include polyclonal antibodies, murine monoclonal antibodies, humanized antibodies derived from murine monoclonal antibodies, and human monoclonal antibodies. Illustrative antibody fragments include F(ab')$_2$, F(ab)$_2$, Fab', Fab, Fv, scFv, and minimal recognition units. The present invention further provides compositions comprising a carrier and a peptide, polypeptide, antibody, or anti-idiotype antibody described herein.

The present invention also provides isolated nucleic acid molecules that encode a Zcytor14 polypeptide, wherein the nucleic acid molecule is selected from the group consisting of: (a) a nucleic acid molecule comprising the nucleotide sequence of SEQ ID NO:3, (b) a nucleic acid molecule encoding an amino acid sequence that comprises either amino acid residues 21 to 677 of SEQ ID NO:2 or amino acid residues 21 to 673 of SEQ ID NO:10, and (c) a nucleic acid molecule that remains hybridized following stringent wash conditions to a nucleic acid molecule comprising the nucleotide sequence of nucleotides 214 to 2184 of SEQ ID NO:1, or the complement of nucleotides 214 to 2184 of SEQ ID NO:1. Illustrative nucleic acid molecules include those in which any difference between the amino acid sequence encoded by nucleic acid molecule (c) and the corresponding amino acid sequence of SEQ ID NO:2 is due to a conservative amino acid substitution. The present invention further contemplates isolated nucleic acid molecules that comprise nucleotides 214 to 2184 of SEQ ID NO:1 or nucleotides 154 to 2184 of SEQ ID NO:1.

The present invention also includes vectors and expression vectors comprising such nucleic acid molecules. Such expression vectors may comprise a transcription promoter, and a transcription terminator, wherein the promoter is operably linked with the nucleic acid molecule, and wherein the nucleic acid molecule is operably linked with the transcription terminator. The present invention further includes recombinant host cells and recombinant viruses comprising these vectors and expression vectors. Illustrative host cells include bacterial, yeast, fungal, insect, mammalian, and plant cells. Recombinant host cells comprising such expression vectors can be used to produce Zcytor14 polypeptides by culturing such recombinant host cells that comprise the expression vector and that produce the Zcytor14 protein, and, optionally, isolating the Zcytor14 protein from the cultured recombinant host cells.

In addition, the present invention provides pharmaceutical compositions comprising a pharmaceutically acceptable carrier and at least one of such an expression vector or recombinant virus comprising such expression vectors. The present invention further includes pharmaceutical compositions, comprising a pharmaceutically acceptable carrier and a polypeptide described herein.

The present invention also contemplates methods for detecting the presence of Zcytor14 RNA in a biological sample, comprising the steps of (a) contacting a Zcytor14 nucleic acid probe under hybridizing conditions with either (i) test RNA molecules isolated from the biological sample, or (ii) nucleic acid molecules synthesized from the isolated RNA molecules, wherein the probe has a nucleotide sequence comprising a portion of the nucleotide sequence of SEQ ID NO:1, or its complement, and (b) detecting the formation of hybrids of the nucleic acid probe and either the test RNA molecules or the synthesized nucleic acid molecules, wherein the presence of the hybrids indicates the presence of Zcytor14 RNA in the biological sample.

The present invention further provides methods for detecting the presence of Zcytor14 polypeptide in a biological sample, comprising the steps of: (a) contacting the biological sample with an antibody or an antibody fragment that specifically binds with a polypeptide consisting of the amino acid sequence of SEQ ID NO:2, wherein the contacting is performed under conditions that allow the binding of the antibody or antibody fragment to the biological sample, and (b) detecting any of the bound antibody or bound antibody fragment. Such an antibody or antibody fragment may further comprise a detectable label selected from the group consisting of radioisotope, fluorescent label, chemiluminescent label, enzyme label, bioluminescent label, and colloidal gold.

The present invention also provides kits for performing these detection methods. For example, a kit for detection of Zcytor14 gene expression may comprise a container that comprises a nucleic acid molecule, wherein the nucleic acid molecule is selected from the group consisting of (a) a nucleic acid molecule comprising the nucleotide sequence of nucleotides 214 to 2184 of SEQ ID NO:1, (b) a nucleic acid molecule comprising the complement of nucleotides 214 to 2184 of the nucleotide sequence of SEQ ID NO:1, (c) a nucleic acid molecule that is a fragment of (a) consisting of at least eight nucleotides, and (d) a nucleic acid molecule that is a fragment of (b) consisting of at least eight nucleotides. Such a kit may also comprise a second container that comprises one or more reagents capable of indicating the presence of the nucleic acid molecule. On the other hand, a kit for detection of Zcytor14 protein may comprise a container that comprises an antibody, or an antibody fragment, that specifically binds with a polypeptide consisting of the amino acid sequence of SEQ ID NO:2.

The present invention also contemplates anti-idiotype antibodies, or anti-idiotype antibody fragments, that specifically bind an antibody or antibody fragment that specifically binds a polypeptide consisting of the amino acid sequence of SEQ ID NO:2 or SEQ ID NO:10.

The present invention also provides isolated nucleic acid molecules comprising a nucleotide sequence that encodes a Zcytor14 secretion signal sequence and a nucleotide sequence that encodes a biologically active polypeptide, wherein the Zcytor14 secretion signal sequence comprises an amino acid sequence of residues 1 to 20 of SEQ ID NO:2. Illustrative biologically active polypeptides include Factor VIIa, proinsulin, insulin, follicle stimulating hormone, tissue type plasminogen activator, tumor necrosis factor, interleukin, colony stimulating factor, interferon, erythropoietin, and thrombopoietin. Moreover, the present invention provides fusion proteins comprising a Zcytor14 secretion signal sequence and a polypeptide, wherein the Zcytor14 secretion signal sequence comprises an amino acid sequence of residues 1 to 20 of SEQ ID NO:2.

The present invention further contemplates isolated nucleic acid molecules that encode an extracellular Zcytor14 domain, wherein the extracellular domain comprises either amino acid residues 21 to 452 of SEQ ID NO:2, or amino acid residues 21 to 435 of SEQ ID NO:10. The present invention also includes isolated polypeptides consisting of either amino acid residues 21 to 452 of SEQ ID NO:2, or amino acid residues 21 to 435 of SEQ ID NO:10, antibodies that specifically bind such polypeptides, and anti-idiotype antibodies that specifically bind with such antibodies.

The present invention also provides fusion proteins, comprising a Zcytor14 extracellular domain and an immunoglobulin moiety, wherein the Zcytor14 extracellular domain comprises either amino acid residues 21 to 452 of SEQ ID NO:2, or amino acid residues 21 to 435 of SEQ ID NO:10. In such fusion proteins, the immunoglobulin moiety may be an immunoglobulin heavy chain constant region, such as a human $F_c$ fragment. The present invention further includes isolated nucleic acid molecules that encode such fusion proteins.

These and other aspects of the invention will become evident upon reference to the following detailed description. In addition, various references are identified below and are incorporated by reference in their entirety.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene,* 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner. For example, a Zcytor14 promoter should stimulate expression of a operably linked gene to a greater extent in thyroid, adrenal gland, prostate, and liver tissues, as opposed to kidney, pancreas, or spleen tissues.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces Zcytor14 from an expression vector. In contrast, Zcytor14 can be produced by a cell that is a "natural source" of Zcytor14, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of a Zcytor14 polypeptide fused with a polypeptide that binds an affinity matrix. Such a fusion protein provides a means to isolate large quantities of Zcytor14 using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9 \text{ M}^{-1}$.

An "anti-idiotype antibody" is an antibody that binds with the variable region domain of an immunoglobulin. In the present context, an anti-idiotype antibody binds with the variable region of an anti-Zcytor14 antibody, and thus, an anti-idiotype antibody mimics an epitope of Zcytor14.

An "antibody fragment" is a portion of an antibody such as $F(ab')_2$, $F(ab)_2$, Fab', Fab, and the like. Regardless of structure, an antibody fragment binds with the same antigen that is recognized by the intact antibody. For example, an anti-Zcytor14 monoclonal antibody fragment binds with an epitope of Zcytor14.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain.

As used herein, a "therapeutic agent" is a molecule or atom, which is conjugated to an antibody moiety to produce a conjugate, which is useful for therapy. Examples of therapeutic agents include drugs, toxins, immunomodulators, chelators, boron compounds, photoactive agents or dyes, and radioisotopes.

A "detectable label" is a molecule or atom, which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

An "immunoconjugate" is a conjugate of an antibody component with a therapeutic agent or a detectable label.

As used herein, the term "antibody fusion protein" refers to a recombinant molecule that comprises an antibody component and a Zcytor14 polypeptide component. Examples of an antibody fusion protein include a protein that comprises a Zcytor14 extracellular domain, and either an Fc domain or an antigen-biding region.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide that will bind a major histocompatibility complex molecule to form an MHC-peptide complex, which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell, which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for Zcytor14" or a "Zcytor14 anti-sense oligonucleotide" is an oligonucleotide having a sequence (a) capable of forming a stable triplex with a portion of the Zcytor14 gene, or (b) capable of forming a stable duplex with a portion of an mRNA transcript of the Zcytor14 gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant Zcytor14 gene" refers to nucleic acid molecules that encode a polypeptide having an amino acid sequence that is a modification of SEQ ID NO:2. Such variants include naturally-occurring polymorphisms of Zcytor14 genes, as well as synthetic genes that contain conservative amino acid substitutions of the amino acid sequence of SEQ ID NO:2. Additional variant forms of Zcytor14 genes are nucleic acid molecules that contain insertions or deletions of the nucleotide sequences described herein. A variant Zcytor14 gene can be identified, for example, by determining whether the gene hybridizes with a nucleic acid molecule having the nucleotide sequence of SEQ ID NO:1, or its complement, under stringent conditions.

Alternatively, variant Zcytor14 genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in *Methods in Gene Biotechnology*, pages 123-151 (CRC Press, Inc. 1997), and Bishop (ed.), *Guide to Human Genome Computing*, 2nd Edition (Academic Press, Inc. 1998)). Particular methods for determining sequence identity are described below.

Regardless of the particular method used to identify a variant Zcytor14 gene or variant Zcytor14 polypeptide, a variant gene or polypeptide encoded by a variant gene may be functionally characterized the ability to bind specifically to an anti-Zcytor14 antibody.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, 0-globin, and myoglobin are paralogs of each other.

The present invention includes functional fragments of Zcytor14 genes. Within the context of this invention, a "functional fragment" of a Zcytor14 gene refers to a nucleic acid molecule that encodes a portion of a Zcytor14 polypeptide, which is a domain described herein or at least specifically binds with an anti-Zcytor14 antibody.

Due to the imprecision of standard analytical methods, molecular weights and lengths of polymers are understood to be approximate values. When such a value is expressed as "about" X or "approximately" X, the stated value of X will be understood to be accurate to 110%.

3. Production of Zcytor14 Genes

Nucleic acid molecules encoding a human Zcytor14 gene can be obtained by screening a human cDNA or genomic library using polynucleotide probes based upon SEQ ID NO:1 or SEQ ID NO:4. These techniques are standard and well-established.

As an illustration, a nucleic acid molecule that encodes a human Zcytor14 gene can be isolated from a cDNA library. In this case, the first step would be to prepare the cDNA library by isolating RNA from a tissue, such as thyroid, adrenal gland, prostate, or liver tissues, using methods well-known to those of skill in the art. In general, RNA isolation techniques must provide a method for breaking cells, a means of inhibiting RNase-directed degradation of RNA, and a method of separating RNA from DNA, protein, and polysaccharide contaminants. For example, total RNA can be isolated by freezing tissue in liquid nitrogen, grinding the frozen tissue with a mortar and pestle to lyse the cells, extracting the ground tissue with a solution of phenol/chloroform to remove proteins, and separating RNA from the remaining impurities by selective precipitation with lithium chloride (see, for example, Ausubel et al. (eds.), *Short Protocols in Molecular Biology*, $3^{rd}$ *Edition*, pages 4-1 to 4-6 (John Wiley & Sons 1995) ["Ausubel (1995)"]; Wu et al., *Methods in Gene Biotechnology*, pages 33-41 (CRC Press, Inc. 1997) ["Wu (1997)"]).

Alternatively, total RNA can be isolated by extracting ground tissue with guanidinium isothiocyanate, extracting with organic solvents, and separating RNA from contaminants using differential centrifugation (see, for example, Chirgwin et al., *Biochemistry* 18:52 (1979); Ausubel (1995) at pages 4-1 to 4-6; Wu (1997) at pages 33-41).

In order to construct a cDNA library, poly(A)$^+$ RNA must be isolated from a total RNA preparation. Poly(A) RNA can be isolated from total RNA using the standard technique of oligo(dT)-cellulose chromatography (see, for example, Aviv and Leder, *Proc. Nat'l Acad. Sci. USA* 69:1408 (1972); Ausubel (1995) at pages 4-11 to 4-12).

Double-stranded cDNA molecules are synthesized from poly(A)$^+$ RNA using techniques well-known to those in the art. (see, for example, Wu (1997) at pages 41-46). Moreover, commercially available kits can be used to synthesize double-stranded cDNA molecules. For example, such kits are available from Life Technologies, Inc. (Gaithersburg, Md.), CLONTECH Laboratories, Inc. (Palo Alto, Calif.), Promega Corporation (Madison, Wis.) and STRATAGENE (La Jolla, Calif.).

Various cloning vectors are appropriate for the construction of a cDNA library. For example, a cDNA library can be prepared in a vector derived from bacteriophage, such as a λgt10 vector. See, for example, Huynh et al., "Constructing and Screening cDNA Libraries in λgt10 and λ gt11," in *DNA Cloning: A Practical Approach Vol. I*, Glover (ed.), page 49 (IRL Press, 1985); Wu (1997) at pages 47-52.

Alternatively, double-stranded cDNA molecules can be inserted into a plasmid vector, such as a PBLUESCRIPT vector (STRATAGENE; La Jolla, Calif.), a LAMDAGEM-4 (Promega Corp.) or other commercially available vectors. Suitable cloning vectors also can be obtained from the American Type Culture Collection (Manassas, Va.).

To amplify the cloned cDNA molecules, the cDNA library is inserted into a prokaryotic host, using standard techniques. For example, a cDNA library can be introduced into competent *E. coli* DH5 cells, which can be obtained, for example, from Life Technologies, Inc. (Gaithersburg, Md.).

A human genomic library can be prepared by means well-known in the art (see, for example, Ausubel (1995) at pages 5-1 to 5-6; Wu (1997) at pages 307-327). Genomic DNA can be isolated by lysing tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient.

DNA fragments that are suitable for the production of a genomic library can be obtained by the random shearing of genomic DNA or by the partial digestion of genomic DNA with restriction endonucleases. Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are well-known in the art (see, for example, Ausubel (1995) at pages 5-1 to 5-6; Wu (1997) at pages 307-327).

Alternatively, human genomic libraries can be obtained from commercial sources such as Research Genetics (Huntsville, Ala.) and the American Type Culture Collection (Manassas, Va.).

A library containing cDNA or genomic clones can be screened with one or more polynucleotide probes based upon SEQ ID NO:1 or SEQ ID NO:4, using standard methods (see, for example, Ausubel (1995) at pages 6-1 to 6-11).

Nucleic acid molecules that encode a human Zcytor14 gene can also be obtained using the polymerase chain reaction (PCR) with oligonucleotide primers having nucleotide sequences that are based upon the nucleotide sequences of the Zcytor14 gene, as described herein. General methods for screening libraries with PCR are provided by, for example, Yu et al., "Use of the Polymerase Chain Reaction to Screen Phage Libraries," in *Methods in Molecular Biology, Vol. 15: PCR Protocols: Current Methods and Applications*, White (ed.), pages 211-215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology, Vol. 15: PCR Protocols: Current Methods and Applications*, White (ed.), pages 317-337 (Humana Press, Inc. 1993).

Anti-Zcytor14 antibodies, produced as described below, can also be used to isolate DNA sequences that encode human Zcytor14 genes from cDNA libraries. For example, the antibodies can be used to screen λgt11 expression libraries, or the antibodies can be used for immunoscreening following hybrid selection and translation (see, for example, Ausubel (1995) at pages 6-12 to 6-16; Margolis et al., "Screening λ expression libraries with antibody and protein probes," in *DNA Cloning 2: Expression Systems, 2nd Edition*, Glover et al. (eds.), pages 1-14 (Oxford University Press 1995)).

As an alternative, a Zcytor14 gene can be obtained by synthesizing nucleic acid molecules using mutually priming long oligonucleotides and the nucleotide sequences described herein (see, for example, Ausubel (1995) at pages 8-8 to 8-9). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology, Vol. 15: PCR Protocols: Current Methods and Applications*, White (ed.), pages 263-268, (Humana Press, Inc. 1993), and Holowachuk et al., *PCR Methods Appl.* 4:299 (1995)).

The nucleic acid molecules of the present invention can also be synthesized with "gene machines" using protocols such as the phosphoramidite method. If chemically-synthesized double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pasternak, *Molecular Biotechnology, Principles and Applications of Recombinant DNA* (ASM Press 1994), Itakura et al., *Ann. Rev. Biochem.* 53:323 (1984), and Climie et al., *Proc. Nat'l Acad. Sci. USA* 87:633 (1990).

The sequence of a Zcytor14 cDNA or Zcytor14 genomic fragment can be determined using standard methods. Zcytor14 polynucleotide sequences disclosed herein can also be used as probes or primers to clone 5' non-coding regions of a Zcytor14 gene. Promoter elements from a Zcytor14 gene can be used to direct the expression of heterologous genes in, for example, thyroid tissue of transgenic animals or patients treated with gene therapy. The identification of genomic fragments containing a Zcytor14 promoter or regulatory element can be achieved using well-established techniques, such as deletion analysis (see, generally, Ausubel (1995)).

Cloning of 5' flanking sequences also facilitates production of Zcytor14 proteins by "gene activation," as disclosed in U.S. Pat. No. 5,641,670. Briefly, expression of an endogenous Zcytor14 gene in a cell is altered by introducing into the Zcytor14 locus a DNA construct comprising at least a targeting sequence, a regulatory sequence, an exon, and an unpaired splice donor site. The targeting sequence is a Zcytor14 5' non-coding sequence that permits homologous recombination of the construct with the endogenous Zcytor14 locus, whereby the sequences within the construct become operably linked with the endogenous Zcytor14 coding sequence. In this way, an endogenous Zcytor14 promoter can be replaced or supplemented with other regulatory sequences to provide enhanced, tissue-specific, or otherwise regulated expression.

4. Production of Zcytor14 Gene Variants

The present invention provides a variety of nucleic acid molecules, including DNA and RNA molecules, that encode the Zcytor14 polypeptides disclosed herein. Those skilled in the art will readily recognize that, in view of the degeneracy of the genetic code, considerable sequence variation is possible among these polynucleotide molecules. SEQ ID NO:3 is a degenerate nucleotide sequence that encompasses all nucleic acid molecules that encode the Zcytor14 polypeptide of SEQ ID NO:2. Those skilled in the art will recognize that the degenerate sequence of SEQ ID NO:3 also provides all RNA sequences encoding SEQ ID NO:2, by substituting U for T. Thus, the present invention contemplates Zcytor14 polypeptide-encoding nucleic acid molecules comprising nucleotide 154 to nucleotide 2229 of SEQ ID NO:1, and their RNA equivalents. Similarly, the Zcytor14-1 degenerate sequence of SEQ ID NO:6 also provides all RNA sequences encoding SEQ ID NO:5, by substituting U for T.

Table 1 sets forth the one-letter codes used within SEQ ID NOs:3 and 6 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
| --- | --- | --- | --- |
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NOs:3 and 6, encompassing all possible codons for a given amino acid, are set forth in Table 2.

TABLE 2

| Amino Acid | One Letter Code | Codons | Degenerate Codon |
| --- | --- | --- | --- |
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |

TABLE 2-continued

| Amino Acid | One Letter Code | Codons | Degenerate Codon |
|---|---|---|---|
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding an amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences of SEQ ID NOs:2, 5, and 10 to 12. Variant sequences can be readily tested for functionality as described herein.

Different species can exhibit "preferential codon usage." In general, see, Grantham et al., *Nucl. Acids Res.* 8:1893 (1980), Haas et al. *Curr. Biol.* 6:315 (1996), Wain-Hobson et al., *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Genet. Dev.* 4:851 (1994), Kane, *Curr. Opin. Biotechnol.* 6:494 (1995), and Makrides, *Microbiol. Rev.* 60:512 (1996). As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed herein serve as a template for optimizing expression of polynucleotides in various cell types and species commonly used in the art and disclosed herein. Sequences containing preferential codons can be tested and optimized for expression in various species, and tested for functionality as disclosed herein.

The present invention further provides variant polypeptides and nucleic acid molecules that represent counterparts from other species (orthologs). These species include, but are not limited to mammalian, avian, amphibian, reptile, fish, insect and other vertebrate and invertebrate species. Of particular interest are Zcytor14 polypeptides from other mammalian species, including mouse, porcine, ovine, bovine, canine, feline, equine, and other primate polypeptides. Orthologs of human Zcytor14 can be cloned using information and compositions provided by the present invention in combination with conventional cloning techniques. For example, a Zcytor14 cDNA can be cloned using mRNA obtained from a tissue or cell type that expresses Zcytor14 as disclosed herein. Suitable sources of mRNA can be identified by probing northern blots with probes designed from the sequences disclosed herein. A library is then prepared from mRNA of a positive tissue or cell line.

A Zcytor14-encoding cDNA can be isolated by a variety of methods, such as by probing with a complete or partial human cDNA or with one or more sets of degenerate probes based on the disclosed sequences. A cDNA can also be cloned using the polymerase chain reaction with primers designed from the representative human Zcytor14 sequences disclosed herein. In addition, a cDNA library can be used to transform or transfect host cells, and expression of the cDNA of interest can be detected with an antibody to Zcytor14 polypeptide.

Those skilled in the art will recognize that the sequence disclosed in SEQ ID NO:1 represents a single allele of human Zcytor14, and that allelic variation and alternative splicing are expected to occur. Allelic variants of this sequence can be cloned by probing cDNA or genomic libraries from different individuals according to standard procedures. Allelic variants of the nucleotide sequences disclosed herein, including those containing silent mutations and those in which mutations result in amino acid sequence changes, are within the scope of the present invention, as are proteins, which are allelic variants of the amino acid sequences disclosed herein. cDNA molecules generated from alternatively spliced mRNAs, which retain the properties of the Zcytor14 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Within certain embodiments of the invention, the isolated nucleic acid molecules can hybridize under stringent conditions to nucleic acid molecules comprising nucleotide sequences disclosed herein. For example, such nucleic acid molecules can hybridize under stringent conditions to nucleic acid molecules comprising the nucleotide sequence of SEQ ID NO:1, to nucleic acid molecules consisting of the nucleotide sequence of nucleotides 154 to 2229 of SEQ ID NO:1, or to nucleic acid molecules comprising a nucleotide sequence complementary to SEQ ID NO:1 or to nucleotides 154 to 2229 of SEQ ID NO:1. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1-1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5-25° C. below the $T_m$ of the hybrid and a hybridization buffer having up to 1 M Na$^+$. Higher degrees of stringency at lower temperatures can be achieved with the addition of formamide, which reduces the $T_m$ of the hybrid about 1° C. for each 1% formamide in the buffer solution. Generally, such stringent conditions include temperatures of 20-70° C. and a hybridization buffer containing up to 6×SSC and 0-50% formamide. A higher degree of stringency can be achieved at temperatures of from 40-70° C. with a hybridization buffer having up to 4×SSC and from 0-50% formamide. Highly stringent conditions typically encompass temperatures of 42-70° C. with a hybridization buffer having up to 1×SSC and 0-50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Those conditions that influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20-25° C. below the calculated $T_m$. For smaller probes, <50 base pairs, hybridization is typically carried out at the $T_m$ or 5-10° C. below. This allows for the maximum rate of hybridization for DNA-DNA and DNA-RNA hybrids.

The length of the polynucleotide sequence influences the rate and stability of hybrid formation. Smaller probe sequences, <50 base pairs, reach equilibrium with complementary sequences rapidly, but may form less stable hybrids. Incubation times of anywhere from minutes to hours can be used to achieve hybrid formation. Longer probe sequences come to equilibrium more slowly, but form more stable complexes even at lower temperatures. Incubations are allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of polynucleotide sequence will effect the thermal stability of the hybrid complex, thereby influencing the choice of hybridization temperature and the ionic strength of the hybridization buffer. A-T pairs are less stable than G-C pairs in aqueous solutions containing sodium chloride. Therefore, the higher the G-C content, the more stable the hybrid. Even distribution of G and C residues within the sequence also contribute positively to hybrid stability. In addition, the base pair composition can be manipulated to alter the $T_m$ of a given sequence. For example, 5-methyldeoxycytidine can be substituted for deoxycytidine and 5-bromodeoxuridine can be substituted for thymidine to increase the $T_m$, whereas 7-deazz-2'-deoxyguanosine can be substituted for guanosine to reduce dependence on $T_m$.

The ionic concentration of the hybridization buffer also affects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a Na$^+$ source, such as SSC (1×SSC: 0.15 M sodium chloride, 15 mM sodium citrate) or SSPE (1×SSPE: 1.8 M NaCl, 10 mM NaH$_2$PO$_4$, 1 mM EDTA, pH 7.7). Typically, hybridization buffers contain from between 10 mM-1 M Na$^+$. The addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

As an illustration, a nucleic acid molecule encoding a variant Zcytor14 polypeptide can be hybridized with a nucleic acid molecule having the nucleotide sequence of SEQ ID NO:1 (or its complement) at 42° C. overnight in a solution comprising 50% formamide, 5×SSC, 50 mM sodium phosphate (pH 7.6), 5× Denhardt's solution (100× Denhardt's solution: 2% (w/v) Ficoll 400, 2% (w/v) polyvinylpyrrolidone, and 2% (w/v) bovine serum albumin), 10% dextran sulfate, and 20 µg/ml denatured, sheared salmon sperm DNA. One of skill in the art can devise variations of these hybridization conditions. For example, the hybridization mixture can be incubated at a higher temperature, such as about 65° C., in a solution that does not contain formamide. Moreover, premixed hybridization solutions are available (e.g., EXPRESSHYB Hybridization Solution from CLONTECH Laboratories, Inc.), and hybridization can be performed according to the manufacturer's instructions.

Following hybridization, the nucleic acid molecules can be washed to remove non-hybridized nucleic acid molecules under stringent conditions, or under highly stringent conditions. Typical stringent washing conditions include washing in a solution of 0.5×-2×SSC with 0.1% sodium dodecyl sulfate (SDS) at 55-65° C. As an illustration, nucleic acid molecules encoding a variant Zcytor14 polypeptide remain hybridized with a nucleic acid molecule consisting of the nucleotide sequence of SEQ ID NO:1 (or its complement) following stringent washing conditions, in which the wash stringency is equivalent to 0.5×-2×SSC with 0.1% SDS at 55-65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×-0.2×SSC with 0.1% sodium dodecyl sulfate (SDS) at 50-65° C. For example, nucleic acid molecules encoding a variant Zcytor14 polypeptide remain hybridized with a nucleic acid molecule consisting of the nucleotide sequence of SEQ ID NO:1 (or its complement) following highly stringent washing conditions, in which the wash stringency is equivalent to 0.1×-0.2×SSC with 0.1% SDS at 50-65° C., including 0.1×SSC with 0.1% SDS at 50° C., or 0.2×SSC with 0.1% SDS at 65° C.

"BLOSUM62" scoring matrix of Henikoff and Henikoff (ibid.) as shown in Table 3 (amino acids are indicated by the standard one-letter codes). The percent identity is then calculated as: ([Total number of identical matches]/[length of the longer sequence plus the number of gaps introduced into the longer sequence in order to align the two sequences])(100).

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The present invention also provides isolated Zcytor14 polypeptides that have a substantially similar sequence identity to the polypeptides of SEQ ID NO:2, or their orthologs. The term "substantially similar sequence identity" is used herein to denote polypeptides having at least 70%, at least 80%, at least 90%, at least 95% or greater than 95% sequence identity to the sequences shown in SEQ ID NO:2, or their orthologs.

The present invention also contemplates Zcytor14 variant nucleic acid molecules that can be identified using two criteria: a determination of the similarity between the encoded polypeptide with the amino acid sequence of SEQ ID NO:2, and a hybridization assay, as described above. Such Zcytor14 variants include nucleic acid molecules (1) that remain hybridized with a nucleic acid molecule consisting of the nucleotide sequence of SEQ ID NO:1 (or its complement) following stringent washing conditions, in which the wash stringency is equivalent to 0.5×-2×SSC with 0.1% SDS at 55-65° C., and (2) that encode a polypeptide having at least 70%, at least 80%, at least 90%, at least 95% or greater than 95% sequence identity to the amino acid sequence of SEQ ID NO:2. Alternatively, Zcytor14 variants can be characterized as nucleic acid molecules (1) that remain hybridized with a nucleic acid molecule consisting of the nucleotide sequence of SEQ ID NO:1 (or its complement) following highly stringent washing conditions, in which the wash stringency is equivalent to 0.1×-0.2×SSC with 0.1% SDS at 50-65° C., and (2) that encode a polypeptide having at least 70%, at least 80%, at least 90%, at least 95% or greater than 95% sequence identity to the amino acid sequence of SEQ ID NO:2.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative Zcytor14 variant. The FASTA algorithm is described by Pearson and Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as described above.

The present invention includes nucleic acid molecules that encode a polypeptide having a conservative amino acid change, compared with an amino acid sequence disclosed herein. For example, variants can be obtained that contain one or more amino acid substitutions of SEQ ID NO:2, in which an alkyl amino acid is substituted for an alkyl amino acid in a Zcytor14 amino acid sequence, an aromatic amino acid is substituted for an aromatic amino acid in a Zcytor14 amino acid sequence, a sulfur-containing amino acid is substituted for a sulfur-containing amino acid in a Zcytor14 amino acid sequence, a hydroxy-containing amino acid is substituted for a hydroxy-containing amino acid in a Zcytor14 amino acid sequence, an acidic amino acid is substituted for an acidic amino acid in a Zcytor14 amino acid sequence, a basic amino acid is substituted for a basic amino acid in a Zcytor14 amino acid sequence, or a dibasic monocarboxylic amino acid is substituted for a dibasic monocarboxylic amino acid in a Zcytor14 amino acid sequence. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Particular variants of Zcytor14 are characterized by having at least 70%, at least 80%, at least 90%, at least 95% or greater than 95% sequence identity to the corresponding amino acid sequence (e.g., SEQ ID NO:2), wherein the variation in amino acid sequence is due to one or more conservative amino acid substitutions.

Conservative amino acid changes in a Zcytor14 gene can be introduced, for example, by substituting nucleotides for the nucleotides recited in SEQ ID NO:1. Such "conservative amino acid" variants can be obtained by oligonucleotide-directed mutagenesis, linker-scanning mutagenesis, mutagenesis using the polymerase chain reaction, and the like (see Ausubel (1995) at pages 8-10 to 8-22; and McPherson (ed.), *Directed Mutagenesis: A Practical Approach* (IRL Press 1991)). A variant Zcytor14 polypeptide can be identified by the ability to specifically bind anti-Zcytor14 antibodies.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci. USA* 90:10145 (1993).

In a second method, translation is carried out in *Xenopus* oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for Zcytor14 amino acid residues.

Essential amino acids in the polypeptides of the present invention can be identified according to procedures known in the art, such as site-directed mutagenesis or alanine-scanning mutagenesis (Cunningham and Wells, *Science* 244:1081 (1989), Bass et al., *Proc. Nat'l Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity to identify amino acid residues that are critical to the activity of the molecule. See also, Hilton et al., *J. Biol. Chem.* 271:4699 (1996).

Although sequence analysis can be used to further define the Zcytor14 ligand binding region, amino acids that play a role in Zcytor14 binding activity can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306 (1992), Smith et al., *J. Mol. Biol.* 224:899(1992), and Wlodaver et al., *FEBS Lett.* 309:59 (1992).

Multiple amino acid substitutions can be made and tested using known methods of mutagenesis and screening, such as those disclosed by Reidhaar-Olson and Sauer (*Science* 241: 53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7:127, (1988)). Moreover, Zcytor14 labeled with biotin or FITC can be used for expression cloning.

Variants of the disclosed Zcytor14 nucleotide and polypeptide sequences can also be generated through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-Zcytor14 antibodies, can be recovered from the host cells and rapidly sequenced using modern equipment. These methods allow the rapid determination of the importance of individual amino acid residues in a polypeptide of interest, and can be applied to polypeptides of unknown structure.

The present invention also includes "functional fragments" of Zcytor14 polypeptides and nucleic acid molecules encoding such functional fragments. Routine deletion analyses of nucleic acid molecules can be performed to obtain functional fragments of a nucleic acid molecule that encodes a Zcytor14 polypeptide. As an illustration, DNA molecules having the nucleotide sequence of SEQ ID NO:1 can be digested with Bal31 nuclease to obtain a series of nested deletions. The fragments are then inserted into expression vectors in proper reading frame, and the expressed polypeptides are isolated and tested for the ability to bind anti-Zcytor14 antibodies. One alternative to exonuclease digestion is to use oligonucleotide-directed mutagenesis to introduce deletions or stop codons to specify production of a desired fragment. Alternatively, particular fragments of a Zcytor14 gene can be synthesized using the polymerase chain reaction.

As an illustration of this general approach, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2-5A synthetase induced by human interferon," in *Biological Interferon Systems, Proceedings of JSIR-TNO Meeting on Interferon Systems*, Cantell (ed.), pages 65-72 (Nijhoff 1987), Herschman, "The EGF Receptor," in *Control of Animal Cell Proliferation*, Vol. 1, Boynton et al., (eds.) pages 169-199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

An example of a functional fragment of a Zcytor14 polypeptide is a soluble form of Zcytor14 that lacks a transmembrane domain. Illustrative Zcytor14 soluble forms include polypeptides consisting of amino acid residues 1 to 452 of SEQ ID NO:2, amino acid residues 21 to 452 of SEQ ID NO:2, amino acid residues 1 to 435 of SEQ ID NO:10, or amino acid residues 21 to 435 of SEQ ID NO:10.

The present invention also contemplates functional fragments of a Zcytor14 gene that have amino acid changes, compared with an amino acid sequence disclosed herein. A variant Zcytor14 gene can be identified on the basis of structure by determining the level of identity with disclosed nucleotide and amino acid sequences, as discussed above. An alternative approach to identifying a variant gene on the basis of structure is to determine whether a nucleic acid molecule encoding a potential variant Zcytor14 gene can hybridize to a nucleic acid molecule comprising a nucleotide sequence, such as SEQ ID NO:1 or SEQ ID NO:4.

The present invention also provides polypeptide fragments or peptides comprising an epitope-bearing portion of a Zcytor14 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein.

Antigenic epitope-bearing peptides and polypeptides can contain at least four to ten amino acids, at least ten to fifteen amino acids, or about 15 to about 30 amino acids of an amino acid sequence disclosed herein. Such epitope-bearing peptides and polypeptides can be produced by fragmenting a Zcytor14 polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology*, Vol. 10, Manson (ed.), pages 105-116 (The Humana Press, Inc. 1992), Price, "Production and Characterization of Synthetic Peptide-Derived Antibodies," in *Monoclonal Antibodies: Production, Engineering, and Clinical Application*, Ritter and Ladyman (eds.), pages 60-84 (Cambridge University Press 1995), and Coligan et al. (eds.), *Current Protocols in Immunology*, pages 9.3.1-9.3.5 and pages 9.4.1-9.4.11 (John Wiley & Sons 1997).

For any Zcytor14 polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise Zcytor14 variants based upon the nucleotide and amino acid sequences described herein. Accordingly, the present invention includes a computer-readable medium encoded with a data structure that provides at least one of the following sequences: SEQ ID NO:1, SEQ ID NO:2, SEQ ID NO:3, SEQ ID NO:4, SEQ ID NO:5, SEQ ID NO:6, SEQ ID NO:8, SEQ ID NO:9, SEQ ID NO:10, SEQ ID NO:1, and SEQ ID NO:12. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

6. Production of Zcytor14 Polypeptides

The polypeptides of the present invention, including full-length polypeptides, functional fragments, and fusion proteins, can be produced in recombinant host cells following conventional techniques. To express a Zcytor14 gene, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene, which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, a Zcytor14 expression vector may comprise a Zcytor14 gene and a secretory sequence derived from any secreted gene.

Zcytor14 proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 (Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (1H-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene, which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Natl. Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice*, Cleland et al. (eds.), pages 163-181 (John Wiley & Sons, Inc. 1996)).

Alternatively, a prokaryotic promoter, such as the bacteriophage T3 RNA polymerase promoter, can be used to control Zcytor14 gene expression in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase, which confers resistance to methotrexate. Other drug resistance genes (e.g., hygromycin resistance, multi-drug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Zcytor14 polypeptides can also be produced by cultured mammalian cells using a viral delivery system. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161 (1994), and Douglas and Curiel, *Science & Medicine* 4:44 (1997)).

Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein (see Garnier et al., *Cytotechnol.* 15:145 (1994)).

Zcytor14 can also be expressed in other higher eukaryotic cells, such as avian, fungal, insect, yeast, or plant cells. The baculovirus system provides an efficient means to introduce cloned Zcytor14 genes into insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila* metallothionein promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the Zcytor14 polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed Zcytor14 polypeptide, for example, a Glu-Glu epitope tag (Grussenmeyer et al., *Proc. Nat'l Acad. Sci.* 82:7952 (1985)). Using a technique known in the art, a transfer vector containing a Zcytor14 gene is transformed into *E. coli*, and screened for bacmids, which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter), which is expressed earlier in the baculovirus infection, and has been shown to be advantageous for expressing secreted proteins (see, for example, Hill-Perkins and Possee, *J. Gen. Virol.* 71:971 (1990), Bonning, et al., *J. Gen. Virol.* 75:1551 (1994), and Chazenbalk and Rapoport, *J. Biol. Chem.* 270:1543 (1995). In such transfer vector constructs, a short or long version of the basic protein promoter can be used. Moreover, transfer vectors can be constructed, which replace the native Zcytor14 secretory signal sequences with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace the native Zcytor14 secretory signal sequence.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sj21AE, and Sj21 (Invitrogen Corporation; San Diego, Calif.), as well as *Drosophila* Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf00 II™ (Life Technologies) or ESF 921$T_m$ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately 2-5× $10^5$ cells to a density of 1-2×$10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology, Volume 7: Gene Transfer and Expression Protocols*, Murray (ed.), pages 147-168 (The Humana Press, Inc. 1991), by Patel et al., "The baculovirus expression system," in *DNA Cloning 2: Expression Systems*, 2nd Edition, Glover et al. (eds.), pages 205-244 (Oxford University Press 1995), by Ausubel (1995) at pages 16-37 to 16-57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183-218 (John Wiley & Sons, Inc. 1996).

Fungal cells, including yeast cells, can also be used to express the genes described herein. Yeast species of particular interest in this regard include *Saccharomyces cerevisiae, Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063,154, 5,139,936, and 4,661,454.

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermon-* dii and *Candida maltosa* are known in the art. See, for example, Gleeson et al., *J. Gen. Microbiol.* 132:3459 (1986), and Cregg, U.S. Pat. No. 4,882,279. *Aspergillus* cells may be utilized according to the methods of McKnight et al., U.S. Pat. No. 4,935,349. Methods for transforming Acremoni m chrysogen m are disclosed by Sumino et al., U.S. Pat. No. 5,162,228. Methods for transforming *Neurospora* are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., Yeast 14:11-23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, host cells can be used in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., *Science* 227:1229 (1985), Klein et al., *Biotechnology* 10:268 (1992), and Miki et al., "Procedures for Introducing Foreign DNA into Plants," in *Methods in Plant Molecular Biology and Biotechnology*, Glick et al. (eds.), pages 67-88 (CRC Press, 1993).

Alternatively, Zcytor14 genes can be expressed in prokaryotic host cells. Suitable promoters that can be used to express Zcytor14 polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of *Bacillus, Streptomyces* promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277 (1987), Watson et al., *Molecular Biology of the Gene, 4th Ed.* (Benjamin Cummins 1987), and by Ausubel et al. (1995).

Illustrative prokaryotic hosts include *E. coli* and *Bacillus subtilus*. Suitable strains of *E. coli* include BL21(DE3), BL21 (DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilis* include BR151, YB886, MI119, MI120, and B170 (see, for example, Hardy, "*Bacillus* Cloning Methods," in *DNA Cloning: A Practical Approach*, Glover (ed.) (IRL Press 1985)).

When expressing a Zcytor14 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), and Georgiou, "Expression of Proteins in Bacteria," in *Protein Engineering: Principles and Practice*, Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning 2: Expression Systems, 2nd Edition*, Glover et al. (eds.), pages 59-92 (Oxford University Press 1995). Established methods for isolating recombinant proteins from a baculovirus system are described by Richardson (ed.), Baculovirus Expression Protocols (The Humana Press, Inc. 1995).

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, *J. Am. Chem. Soc.* 85:2149 (1963), Stewart et al., "Solid Phase Peptide Synthesis" (2nd Edition), (Pierce Chemical Co. 1984), Bayer and Rapp, *Chem. Pept. Prot.* 3:3 (1986), Atherton et al.,

*Solid Phase Peptide Synthesis: A Practical Approach* (IRL Press 1989), Fields and Colowick, "Solid-Phase Peptide Synthesis," *Methods in Enzymology Volume* 289 (Academic Press 1997), and Lloyd-Williams et al., *Chemical Approaches to the Synthesis of Peptides and Proteins* (CRC Press, Inc. 1997)). Variations in total chemical synthesis strategies, such as "native chemical ligation" and "expressed protein ligation" are also standard (see, for example, Dawson et al., *Science* 266:776 (1994), Hackeng et al., *Proc. Nat'l Acad. Sci. USA* 94:7845 (1997), Dawson, *Methods Enzymol.* 287: 34 (1997), Muir et a, *Proc. Nat'l Acad. Sci. USA* 95:6705 (1998), and Severinov and Muir, *J. Biol. Chem.* 273:16205 (1998)).

Peptides and polypeptides of the present invention comprise at least six, at least nine, or at least 15 contiguous amino acid residues of SEQ ID NO:2, SEQ ID NO:5, SEQ ID NO:10, SEQ ID NO:11, or SEQ ID NO:12. For example, the present invention includes polypeptides comprising, or consisting of, 15 contiguous amino acids of the following amino acid sequences: amino acid residues 21 to 452 of the amino acid sequence of SEQ ID NO:2, amino acid residues 21 to 435 of the amino acid sequence of SEQ ID NO:10, amino acid residues 474 to 677 of SEQ ID NO:2, or amino acid residues 457 to 673 of SEQ ID NO:10. Within certain embodiments of the invention, the polypeptides comprise 20, 30, 40, 50, 100, or more contiguous residues of these amino acid sequences. As an illustration, the present invention includes polypeptides comprising, or consisting of, 30 or 40 contiguous amino acids of the following amino acid sequences: amino acid residues 21 to 452 of the amino acid sequence of SEQ ID NO:2, amino acid residues 21 to 435 of the amino acid sequence of SEQ ID NO:10, amino acid residues 474 to 677 of SEQ ID NO:2, or amino acid residues 457 to 673 of SEQ ID NO:10. Nucleic acid molecules encoding such peptides and polypeptides are useful as polymerase chain reaction primers and probes.

7. Production of Zcytor14 Fusion Proteins and Conjugates

One general class of Zcytor14 analogs are variants having an amino acid sequence that is a mutation of the amino acid sequence disclosed herein. Another general class of Zcytor14 analogs is provided by anti-idiotype antibodies, and fragments thereof, as described below. Moreover, recombinant antibodies comprising anti-idiotype variable domains can be used as analogs (see, for example, Monfardini et al., *Proc. Assoc. Am. Physicians* 108:420 (1996)). Since the variable domains of anti-idiotype Zcytor14 antibodies mimic Zcytor14, these domains can provide Zcytor14 binding activity. Methods of producing anti-idiotypic catalytic antibodies are known to those of skill in the art (see, for example, Joron et al., *Ann. NY Acad. Sci.* 672:216 (1992), Friboulet et al., *Appl. Biochem. Biotechnol.* 47:229 (1994), and Avalle et al., *Ann. NY Acad. Sci.* 864:118 (1998)).

Another approach to identifying Zcytor14 analogs is provided by the use of combinatorial libraries. Methods for constructing and screening phage display and other combinatorial libraries are provided, for example, by Kay et al., *Phage Display of Peptides and Proteins* (Academic Press 1996), Verdine, U.S. Pat. No. 5,783,384, Kay, et. al., U.S. Pat. No. 5,747,334, and Kauffiman et al., U.S. Pat. No. 5,723,323.

Zcytor14 polypeptides have both in vivo and in vitro uses. As an illustration, a soluble form of Zcytor14 can be added to cell culture medium to inhibit the effects of the Zcytor14 ligand produced by the cultured cells.

Fusion proteins of Zcytor14 can be used to express Zcytor14 in a recombinant host, and to isolate the produced Zcytor14. As described below, particular Zcytor14 fusion proteins also have uses in diagnosis and therapy. One type of fusion protein comprises a peptide that guides a Zcytor14 polypeptide from a recombinant host cell. To direct a Zcytor14 polypeptide into the secretory pathway of a eukaryotic host cell, a secretory signal sequence (also known as a signal peptide, a leader sequence, prepro sequence or pre sequence) is provided in the Zcytor14 expression vector. While the secretory signal sequence may be derived from Zcytor14, a suitable signal sequence may also be derived from another secreted protein or synthesized de novo. The secretory signal sequence is operably linked to a Zcytor14-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of Zcytor14 or another protein produced by mammalian cells (e.g., tissue-type plasminogen activator signal sequence, as described, for example, in U.S. Pat. No. 5,641,655) is useful for expression of Zcytor14 in recombinant mammalian hosts, a yeast signal sequence is preferred for expression in yeast cells. Examples of suitable yeast signal sequences are those derived from yeast mating phermone α-factor (encoded by the MFα1 gene), invertase (encoded by the SUC2 gene), or acid phosphatase (encoded by the PHO5 gene). See, for example, Romanos et al., "Expression of Cloned Genes in Yeast," in *DNA Cloning 2: A Practical Approach,* $2^{nd}$ Edition, Glover and Hames (eds.), pages 123-167 (Oxford University Press 1995).

In bacterial cells, it is often desirable to express a heterologous protein as a fusion protein to decrease toxicity, increase stability, and to enhance recovery of the expressed protein. For example, Zcytor14 can be expressed as a fusion protein comprising a glutathione S-transferase polypeptide. Glutathione S-transferease fusion proteins are typically soluble, and easily purifiable from *E. coli* lysates on immobilized glutathione columns. In similar approaches, a Zcytor14 fusion protein comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in *E. coli* Using Plasmid Vectors and Purification of Specific Polyclonal Antibodies," in *DNA Cloning 2: A Practical Approach,* $2^{nd}$ Edition, Glover and Hames (Eds.), pages 15-58 (Oxford University Press 1995). In addition, commercially available expression systems are available. For example, the PINPOINT Xa protein purification system (Promega Corporation; Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene*

186:55 (1997). Nucleic acid molecules encoding such peptide tags are available, for example, from Sigma-Aldrich Corporation (St. Louis, Mo.).

The present invention also contemplates that the use of the secretory signal sequence contained in the Zcytor14 polypeptides of the present invention to direct other polypeptides into the secretory pathway. A signal fusion polypeptide can be made wherein a secretory signal sequence derived from amino acid residues 1 to 20 of SEQ ID NO:2 is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in a transgenic animal or in a cultured recombinant host to direct peptides through the secretory pathway. With regard to the latter, exemplary polypeptides include pharmaceutically active molecules such as Factor VIIa, proinsulin, insulin, follicle stimulating hormone, tissue type plasminogen activator, tumor necrosis factor, interleukins (e.g., interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, and IL-18), colony stimulating factors (e.g., granulocyte-colony stimulating factor, and granulocyte macrophage-colony stimulating factor), interferons (e.g., interferons-α, -β, -γ, -ω, -δ, -□, and -τ), the stem cell growth factor designated "S1 factor," erythropoietin, and thrombopoietin. The Zcytor14 secretory signal sequence contained in the fusion polypeptides of the present invention is preferably fused amino-terminally to an additional peptide to direct the additional peptide into the secretory pathway. Fusion proteins comprising a Zcytor14 secretory signal sequence can be constructed using standard techniques.

Another form of fusion protein comprises a Zcytor14 polypeptide and an immunoglobulin heavy chain constant region, typically an $F_C$ fragment, which contains two or three constant region domains and a hinge region but lacks the variable region. As an illustration, Chang et al., U.S. Pat. No. 5,723,125, describe a fusion protein comprising a human interferon and a human immunoglobulin Fc fragment. The C-terminal of the interferon is linked to the N-terminal of the Fc fragment by a peptide linker moiety. An example of a peptide linker is a peptide comprising primarily a T cell inert sequence, which is immunologically inert. An exemplary peptide linker has the amino acid sequence: GGSGG SGGGG SGGGG S (SEQ ID NO:7). In this fusion protein, a preferred Fc moiety is a human γ4 chain, which is stable in solution and has little or no complement activating activity. Accordingly, the present invention contemplates a Zcytor14 fusion protein that comprises a Zcytor14 moiety and a human Fc fragment, wherein the C-terminus of the Zcytor14 moiety is attached to the N-terminus of the Fc fragment via a peptide linker, such as a peptide consisting of the amino acid sequence of SEQ ID NO:7. The Zcytor14 moiety can be a Zcytor14 molecule or a fragment thereof. For example, a fusion protein can comprise a fragment of Zcytor14 that contains the extracellular domain (e.g., a soluble Zcytor14 receptor) and an Fc fragment (e.g., a human Fc fragment).

In another variation, a Zcytor14 fusion protein comprises an IgG sequence, a Zcytor14 moiety covalently joined to the aminoterminal end of the IgG sequence, and a signal peptide that is covalently joined to the aminoterminal of the Zcytor14 moiety, wherein the IgG sequence consists of the following elements in the following order: a hinge region, a $CH_2$ domain, and a $CH_3$ domain. Accordingly, the IgG sequence lacks a $CH_1$ domain. The Zcytor14 moiety displays a Zcytor14 activity, as described herein, such as the ability to bind with a Zcytor14 ligand. This general approach to producing fusion proteins that comprise both antibody and nonantibody portions has been described by LaRochelle et al., EP 742830 (WO 95/21258).

Fusion proteins comprising a Zcytor14 moiety and an Fc moiety can be used, for example, as an in vitro assay tool. For example, the presence of a Zcytor14 ligand in a biological sample can be detected using a Zcytor14-immunoglobulin fusion protein, in which the Zcytor14 moiety is used to bind the ligand, and a macromolecule, such as Protein A or anti-Fc antibody, is used to bind the fusion protein to a solid support. Such systems can be used to identify agonists and antagonists that interfere with the binding of a Zcytor14 ligand to its receptor.

Other examples of antibody fusion proteins include polypeptides that comprise an antigen-binding domain and a Zcytor14 fragment that contains a Zcytor14 extracellular domain. Such molecules can be used to target particular tissues for the benefit of Zcytor14 binding activity.

The present invention further provides a variety of other polypeptide fusions. For example, part or all of a domain(s) conferring a biological function can be swapped between Zcytor14 of the present invention with the functionally equivalent domain(s) from another member of the cytokine receptor family. Polypeptide fusions can be expressed in recombinant host cells to produce a variety of Zcytor14 fusion analogs. A Zcytor14 polypeptide can be fused to two or more moieties or domains, such as an affinity tag for purification and a targeting domain. Polypeptide fusions can also comprise one or more cleavage sites, particularly between domains. See, for example, Tuan et al., *Connective Tissue Research* 34:1 (1996).

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. General methods for enzymatic and chemical cleavage of fusion proteins are described, for example, by Ausubel (1995) at pages 16-19 to 16-25.

Zcytor14 polypeptides can be used to identify and to isolate Zcytor14 ligands. Zcytor14 extracellular domain (e.g., amino acid residues 1 to 452, or 21 to 452 of SEQ ID NO:2) and other forms of a soluble Zcytor14 receptor, are particularly useful for these methods. For example, proteins and peptides of the present invention can be immobilized on a column and used to bind ligands from a biological sample that is run over the column (Hermanson et al. (eds.), *Immobilized Affinity Ligand Techniques*, pages 195-202 (Academic Press 1992)).

The activity of a Zcytor14 polypeptide can be observed by a silicon-based biosensor microphysiometer, which measures the extracellular acidification rate or proton excretion associated with receptor binding and subsequent physiologic cellular responses. An exemplary device is the CYTOSENSOR Microphysiometer manufactured by Molecular Devices, Sunnyvale, Calif. A variety of cellular responses, such as cell proliferation, ion transport, energy production, inflammatory response, regulatory and receptor activation, and the like, can be measured by this method (see, for example, McConnell et al., *Science* 257:1906 (1992), Pitchford et al., *Meth. Enzymol.* 228:84 (1997), Arimilli et al., *J. Immunol. Meth.* 212:49 (1998), Van Liefde et al., *Eur. J. Pharmacol.* 346:87 (1998)).

The microphysiometer can be used for assaying eukaryotic, prokaryotic, adherent, or non-adherent cells. By measuring extracellular acidification changes in cell media over time, the microphysiometer directly measures cellular responses to various stimuli, including agonists, ligands, or antagonists of Zcytor14.

The microphysiometer can be used to measure responses of an Zcytor14-expressing eukaryotic cell, compared to a control eukaryotic cell that does not express Zcytor14 polypeptide. Suitable cells responsive to Zcytor14-modulating stimuli include recombinant host cells comprising a Zcytor14 expression vector, and cells that naturally express Zcytor14. Extracellular acidification provides one measure for a Zcytor14-modulated cellular response. In addition, this approach can be used to identify ligands, agonists, and antagonists of Zcytor14 ligand. For example, a molecule can be identified as an agonist of Zcytor14 ligand by providing cells that express a Zcytor14 polypeptide, culturing a first portion of the cells in the absence of the test compound, culturing a second portion of the cells in the presence of the test compound, and determining whether the second portion exhibits a cellular response, in comparison with the first portion.

Alternatively, a solid phase system can be used to identify a Zcytor14 ligand, or an agonist or antagonist of a Zcytor14 ligand. For example, a Zcytor14 polypeptide or Zcytor14 fusion protein can be immobilized onto the surface of a receptor chip of a commercially available biosensor instrument (BIACORE, Biacore AB; Uppsala, Sweden). The use of this instrument is disclosed, for example, by Karlsson, *Immunol. Methods* 145:229 (1991), and Cunningham and Wells, *J. Mol. Biol.* 234:554 (1993).

In brief, a Zcytor14 polypeptide or fusion protein is covalently attached, using amine or sulfhydryl chemistry, to dextran fibers that are attached to gold film within a flow cell. A test sample is then passed through the cell. If a ligand is present in the sample, it will bind to the immobilized polypeptide or fusion protein, causing a change in the refractive index of the medium, which is detected as a change in surface plasmon resonance of the gold film. This system allows the determination of on- and off-rates, from which binding affinity can be calculated, and assessment of stoichiometry of binding. This system can also be used to examine antibody-antigen interactions, and the interactions of other complement/anti-complement pairs.

Zcytor14 binding domains can be further characterized by physical analysis of structure, as determined by such techniques as nuclear magnetic resonance, crystallography, electron diffraction or photoaffinity labeling, in conjunction with mutation of putative contact site amino acids of Zcytor14 ligand agonists. See, for example, de Vos et al., Science 255: 306 (1992), Smith et al., *J. Mol. Biol.* 224:899 (1992), and Wlodaver et al., *FEBS Lett.* 309:59 (1992).

The present invention also contemplates chemically modified Zcytor14 compositions, in which a Zcytor14 polypeptide is linked with a polymer. Illustrative Zcytor14 polypeptides are soluble polypeptides that lack a functional transmembrane domain. Typically, the polymer is water soluble so that the Zcytor14 conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, or mono-(C1-C10) alkoxy, or aryloxy derivatives thereof (see, for example, Harris, et al., U.S. Pat. No. 5,252,714). The polymer may be branched or unbranched. Moreover, a mixture of polymers can be used to produce Zcytor14 conjugates.

Zcytor14 conjugates used for therapy can comprise pharmaceutically acceptable water-soluble polymer moieties. Suitable water-soluble polymers include polyethylene glycol (PEG), monomethoxy-PEG, mono-(C1-C10)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A Zcytor14 conjugate can also comprise a mixture of such water-soluble polymers.

One example of a Zcytor14 conjugate comprises a Zcytor14 moiety and a polyalkyl oxide moiety attached to the N-terminus of the Zcytor14 moiety. PEG is one suitable polyalkyl oxide. As an illustration, Zcytor14 can be modified with PEG, a process known as "PEGylation." PEGylation of Zcytor14 can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, Zcytor14 conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with a Zcytor14 polypeptide. An example of an activated PEG ester is PEG esterified to N-hydroxysuccinimide. As used herein, the term "acylation" includes the following types of linkages between Zcytor14 and a water soluble polymer: amide, carbamate, urethane, and the like. Methods for preparing PEGylated Zcytor14 by acylation will typically comprise the steps of (a) reacting a Zcytor14 polypeptide with PEG (such as a reactive ester of an aldehyde derivative of PEG) under conditions whereby one or more PEG groups attach to Zcytor14, and (b) obtaining the reaction product(s). Generally, the optimal reaction conditions for acylation reactions will be determined based upon known parameters and desired results. For example, the larger the ratio of PEG:Zcytor14, the greater the percentage of polyPEGylated Zcytor14 product.

The product of PEGylation by acylation is typically a polyPEGylated Zcytor14 product, wherein the lysine ε-amino groups are PEGylated via an acyl linking group. An example of a connecting linkage is an amide. Typically, the resulting Zcytor14 will be at least 95% mono-, di-, or tri-pegylated, although some species with higher degrees of PEGylation may be formed depending upon the reaction conditions. PEGylated species can be separated from unconjugated Zcytor14 polypeptides using standard purification methods, such as dialysis, ultrafiltration, ion exchange chromatography, affinity chromatography, and the like.

PEGylation by alkylation generally involves reacting a terminal aldehyde derivative of PEG with Zcytor14 in the presence of a reducing agent. PEG groups are preferably attached to the polypeptide via a —$CH_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of Zcytor14 monopolymer conjugates.

Reductive alkylation to produce a substantially homogenous population of monopolymer Zcytor14 conjugate molecule can comprise the steps of: (a) reacting a Zcytor14 polypeptide with a reactive PEG under reductive alkylation conditions at a pH suitable to permit selective modification of the α-amino group at the amino terminus of the Zcytor14, and (b) obtaining the reaction product(s). The reducing agent used for reductive alkylation should be stable in aqueous solution and preferably be able to reduce only the Schiff base formed in the initial process of reductive alkylation. Preferred reducing agents include sodium borohydride, sodium cyanoborohydride, dimethylamine borane, trimethylamine borane, and pyridine borane.

For a substantially homogenous population of monopolymer Zcytor14 conjugates, the reductive alkylation reaction conditions are those which permit the selective attachment of the water soluble polymer moiety to the N-terminus of Zcytor14. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer:Zcytor14 need not be as large because more reactive groups are available. Typically, the pH will fall within the range of 3-9, or 3-6.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to Zcytor14 will generally be in the range of 1:1 to 100:1. Typically, the molar ratio of water-soluble polymer to Zcytor14 will be 1:1 to 20:1 for polyPEGylation, and 1:1 to 5:1 for monoPEGylation.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738,846, Nieforth et al., *Clin. Pharmacol. Ther.* 59:636 (1996), Monkarsh et al., *Anal. Biochem.* 247:434 (1997)).

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

8. Isolation of Zcytor14 Polypeptides

The polypeptides of the present invention can be purified to at least about 80% purity, to at least about 90% purity, to at least about 95% purity, or even greater than 95% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, a purified polypeptide is substantially free of other polypeptides, particularly other polypeptides of animal origin.

Fractionation and/or conventional purification methods can be used to obtain preparations of Zcytor14 purified from natural sources (e.g., prostate or thyroid tissue), synthetic Zcytor14 polypeptides, and recombinant Zcytor14 polypeptides and fusion Zcytor14 polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

Additional variations in Zcytor14 isolation and purification can be devised by those of skill in the art. For example, anti-Zcytor14 antibodies, obtained as described below, can be used to isolate large quantities of protein by immunoaffinity purification.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), *Meth. Enzymol.* 182:529 (1990)). Within additional embodiments of the invention, a fusion of the polypeptide of interest and an affinity tag (e.g., maltose-binding protein, an immunoglobulin domain) may be constructed to facilitate purification.

Zcytor14 polypeptides or fragments thereof may also be prepared through chemical synthesis, as described above. Zcytor14 polypeptides may be monomers or multimers; glycosylated or non-glycosylated; PEGylated or non-PEGylated; and may or may not include an initial methionine amino acid residue.

9. Production of Antibodies to Zcytor14 Proteins

Antibodies to Zcytor14 can be obtained, for example, using the product of a Zcytor14 expression vector or Zcytor14 isolated from a natural source as an antigen. Particularly useful anti-Zcytor14 antibodies "bind specifically" with Zcytor14. Antibodies are considered to be specifically binding if the antibodies exhibit at least one of the following two properties: (1) antibodies bind to Zcytor14 with a threshold level of binding activity, and (2) antibodies do not significantly cross-react with polypeptides related to Zcytor14.

With regard to the first characteristic, antibodies specifically bind if they bind to a Zcytor14 polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51:660 (1949)). With regard to the second characteristic, antibodies do not significantly cross-react with related polypeptide molecules, for example, if they detect Zcytor14, but not presently known polypeptides using a standard Western blot analysis. Examples of known related polypeptides include known cytokine receptors.

Anti-Zcytor14 antibodies can be produced using antigenic Zcytor14 epitope-bearing peptides and polypeptides. Antigenic epitope-bearing peptides and polypeptides of the present invention contain a sequence of at least nine, or between 15 to about 30 amino acids contained within SEQ ID NO:2 or another amino acid sequence disclosed herein. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with Zcytor14. It is desirable that the amino acid sequence of the epitope-bearing peptide is selected to provide substantial solubility in aqueous solvents (i.e., the sequence includes relatively hydrophilic residues, while hydrophobic residues are preferably avoided). Moreover, amino acid sequences containing proline residues may be also be desirable for antibody production.

As an illustration, potential antigenic sites in Zcytor14 were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for protein structural prediction. Briefly, the Hopp-Woods method, Hopp et al., *Proc. Nat'l Acad. Sci. USA* 78:3824 (1981), was first used to identify amino acid sequences representing areas of greatest local hydrophilicity (parameter: seven residues averaged). In the second step, Emini's method, Emini et al., *J. Virology* 55:836 (1985), was used to calculate surface probabilities (parameter: surface decision threshold (0.6)=1). Third, the Karplus-Schultz method, Karplus and Schultz, *Naturwissenschaften* 72:212 (1985), was used to predict backbone chain flexibility (parameter: flexibility threshold (0.2)=1). In the fourth and fifth steps of the analysis, secondary structure predictions were applied to the data using the methods of Chou-Fasman, Chou, "Prediction of Protein Structural Classes from Amino Acid Composition," in *Prediction of Protein Structure and the Principles of Protein Conformation*, Fasman (ed.), pages 549-586 (Plenum Press 1990), and Garnier-Robson, Garnier et al., *J. Mol. Biol.* 120: 97 (1978) (Chou-Fasman parameters: conformation table=64 proteins; α region threshold=103; β region threshold=105; Garnier-Robson parameters: α and β decision constants=0). In the sixth subroutine, flexibility parameters and hydropathy/solvent accessibility factors were combined to determine a surface contour value, designated as the "antigenic index." Finally, a peak broadening function was applied to the antigenic index, which broadens major surface peaks by adding 20, 40, 60, or 80% of the respective peak value to account for additional free energy derived from the mobility of surface regions relative to interior regions. This calculation was not applied, however, to any major peak that resides in a helical region, since helical regions tend to be less flexible.

The results of this analysis indicated that the following amino acid sequences of SEQ ID NO:2 would provide suitable antigenic peptides: amino acids 26 to 33 ("antigenic peptide 1"), amino acids 41 to 46 ("antigenic peptide 2"), 74 to 81 ("antigenic peptide 3"), amino acids 95 to 105 ("antigenic peptide 4"), amino acids 109 to 119 ("antigenic peptide 5"), amino acids 95 to 119 ("antigenic peptide 6"), amino acids 178 to 185 ("antigenic peptide 7"), amino acids 200 to 206 ("antigenic peptide 8"), amino acids 231 to 238 ("antigenic peptide 9"), amino acids 231 to 241 ("antigenic peptide 10"), amino acids 264 to 270 ("antigenic peptide 11"), amino acids 274 to 281 ("antigenic peptide 12"), amino acids 317 to 324 ("antigenic peptide 13"), amino acids 357 to 363 ("antigenic peptide 14"), amino acids 384 to 392 ("antigenic peptide 15"), amino acids 398 to 411 ("antigenic peptide 16"), amino acids 405 to 411 ("antigenic peptide 17"), amino acids 423 to 429 ("antigenic peptide 18"), and amino acids 434 to 439 ("antigenic peptide 19"). The present invention contemplates the use of any one of antigenic peptides 1 to 19 to generate antibodies to Zcytor14. The present invention also contemplates polypeptides comprising at least one of antigenic peptides 1 to 19.

Polyclonal antibodies to recombinant Zcytor14 protein or to Zcytor14 isolated from natural sources can be prepared using methods well-known to those of skill in the art. See, for example, Green et al., "Production of Polyclonal Antisera," in *Immunochemical Protocols* (Manson, ed.), pages 1-5 (Humana Press 1992), and Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995). The immunogenicity of a Zcytor14 polypeptide can be increased through the use of an adjuvant, such as alum (aluminum hydroxide) or Freund's complete or incomplete adjuvant. Polypeptides useful for immunization also include fusion polypeptides, such as fusions of Zcytor14 or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, guinea pigs, goats, or sheep, an anti-Zcytor14 antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310 (1990).

Alternatively, monoclonal anti-Zcytor14 antibodies can be generated. Rodent mono-clonal antibodies to specific antigens may be obtained by methods known to those skilled in the art (see, for example, Kohler et al., *Nature* 256:495 (1975), Coligan et al. (eds.), *Current Protocols in Immunology*, Vol. 1, pages 2.5.1-2.6.7 (John Wiley & Sons 1991) ["Coligan"], Picksley et al., "Production of monoclonal antibodies against proteins expressed in *E. coli*," in *DNA Cloning 2: Expression Systems, 2nd Edition*, Glover et al. (eds.), page 93 (Oxford University Press 1995)).

Briefly, monoclonal antibodies can be obtained by injecting mice with a composition comprising a Zcytor14 gene product, verifying the presence of antibody production by removing a serum sample, removing the spleen to obtain B-lymphocytes, fusing the B-lymphocytes with myeloma cells to produce hybridomas, cloning the hybridomas, selecting positive clones that produce antibodies to the antigen, culturing the clones that produce antibodies to the antigen, and isolating the antibodies from the hybridoma cultures.

In addition, an anti-Zcytor14 antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, Vol. 10, pages 79-104 (The Humana Press, Inc. 1992)).

For particular uses, it may be desirable to prepare fragments of anti-Zcytor14 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology* Vol. 1, page 422 (Academic Press 1967), and by Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains, which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector, which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11:1271 (1993), and Sandhu, supra).

As an illustration, a scFV can be obtained by exposing lymphocytes to Zcytor14 polypeptide in vitro, and selecting antibody display libraries in phage or similar vectors (for instance, through use of immobilized or labeled Zcytor14 protein or peptide). Genes encoding polypeptides having potential Zcytor14 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides, which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the Zcytor14 sequences disclosed herein to identify proteins which bind to Zcytor14.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in Monoclonal Antibodies: Production, Engineering and Clinical Application, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-Zcytor14 antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989). Techniques for producing humanized monoclonal antibodies are described, for example, by Jones et al., *Nature* 321:522 (1986), Carter et al., *Proc. Nat'l Acad. Sci. USA* 89:4285 (1992), Sandhu, *Crit. Rev. Biotech.* 12:437 (1992), Singer et al., *J. Immun.* 150:2844 (1993), Sudhir (ed.), *Antibody Engineering Protocols* (Humana Press, Inc. 1995), Kelley, "Engineering Therapeutic Antibodies," in *Protein Engineering: Principles and Practice*, Cleland et al. (eds.), pages 399-434 (John Wiley & Sons, Inc. 1996), and by Queen et al., U.S. Pat. No. 5,693,762 (1997).

Polyclonal anti-idiotype antibodies can be prepared by immunizing animals with anti-Zcytor14 antibodies or antibody fragments, using standard techniques. See, for example, Green et al., "Production of Polyclonal Antisera," in *Methods In Molecular Biology: Immunochemical Protocols*, Manson (ed.), pages 1-12 (Humana Press 1992). Also, see Coligan at pages 2.4.1-2.4.7. Alternatively, monoclonal anti-idiotype antibodies can be prepared using anti-Zcytor14 antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

10. Use of Zcytor14 Nucleotide Sequences to Detect Gene Expression and Gene Structure Nucleic acid molecules can be used to detect the expression of a Zcytor14 gene in a biological sample. Certain probe molecules include double-stranded nucleic acid molecules comprising the nucleotide sequence of SEQ ID NO:1, SEQ ID NO:4, or a portion thereof, as well as single-stranded nucleic acid molecules having the complement of the nucleotide sequence of SEQ ID NO:1, SEQ ID NO:4, or a portion thereof. Probe molecules may be DNA, RNA, oligonucleotides, and the like. As used herein, the term "portion" refers to at least eight nucleotides to at least 20 or more nucleotides. Certain probes bind with regions of the Zcytor14 gene that have a low sequence similarity to comparable regions in other cytokine receptor genes.

In a basic assay, a single-stranded probe molecule is incubated with RNA, isolated from a biological sample, under conditions of temperature and ionic strength that promote base pairing between the probe and target Zcytor14 RNA species. After separating unbound probe from hybridized molecules, the amount of hybrids is detected.

Well-established hybridization methods of RNA detection include northern analysis and dot/slot blot hybridization (see, for example, Ausubel (1995) at pages 4-1 to 4-27, and Wu et al. (eds.), "Analysis of Gene Expression at the RNA Level," in *Methods in Gene Biotechnology*, pages 225-239 (CRC Press, Inc. 1997)). Nucleic acid probes can be detectably labeled with radioisotopes such as $^{32}P$ or $^{35}S$. Alternatively, Zcytor14 RNA can be detected with a nonradioactive hybridization method (see, for example, Isaac (ed.), *Protocols for Nucleic Acid Analysis by Nonradioactive Probes* (Humana Press, Inc. 1993)). Typically, nonradioactive detection is achieved by enzymatic conversion of chromogenic or chemiluminescent substrates. Illustrative nonradioactive moieties include biotin, fluorescein, and digoxigenin.

Zcytor14 oligonucleotide probes are also useful for in vivo diagnosis. As an illustration, $^{18}F$-labeled oligonucleotides can be administered to a subject and visualized by positron emission tomography (Tavitian et al., *Nature Medicine* 4:467 (1998)).

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

PCR primers can be designed to amplify a portion of the Zcytor14 gene that has a low sequence similarity to a comparable region in other proteins, such as other cytokine receptor proteins.

One variation of PCR for diagnostic assays is reverse transcriptase-PCR (RT-PCR). In the RT-PCR technique, RNA is isolated from a biological sample, reverse transcribed to cDNA, and the cDNA is incubated with Zcytor14 primers (see, for example, Wu et al. (eds.), "Rapid Isolation of Specific cDNAs or Genes by PCR," in *Methods in Gene Biotechnology*, pages 15-28 (CRC Press, Inc. 1997)). PCR is then performed and the products are analyzed using standard techniques.

As an illustration, RNA is isolated from biological sample using, for example, the guanidinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or Zcytor14 anti-sense oligomers. Oligo-dT primers offer the advantage that various mRNA nucleotide sequences are amplified that can provide control target sequences. Zcytor14 sequences are amplified by the polymerase chain reaction using two flanking oligonucleotide primers that are typically 20 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled Zcytor14 probe, and examined by autoradiography. Additional alternative approaches include the use of digoxigenin-labeled deoxyribonucleic acid triphosphates to provide chemiluminescence detection, and the C-TRAK colorimetric assay.

Another approach for detection of Zcytor14 expression is cycling probe technology (CPT), in which a single-stranded DNA target binds with an excess of DNA-RNA-DNA chimeric probe to form a complex, the RNA portion is cleaved with RNAase H, and the presence of cleaved chimeric probe is detected (see, for example, Beggs et al., *J. Clin. Microbiol.* 34:2985 (1996), Bekkaoui et al., *Biotechniques* 20:240 (1996)). Alternative methods for detection of Zcytor14 sequences can utilize approaches such as nucleic acid sequence-based amplification, cooperative amplification of templates by cross-hybridization, and the ligase chain reaction (see, for example, Marshall et al., U.S. Pat. No. 5,686,272 (1997), Dyer et al., *J. Virol. Methods* 60:161 (1996), Ehricht et al., *Eur. J. Biochem.* 243:358 (1997), and Chadwick et al., *J. Virol. Methods* 70:59 (1998)). Other standard methods are known to those of skill in the art.

Zcytor14 probes and primers can also be used to detect and to localize Zcytor14 gene expression in tissue samples. Methods for such in situ hybridization are well-known to those of skill in the art (see, for example, Choo (ed.), *In Situ Hybridization Protocols* (Humana Press, Inc. 1994), Wu et al. (eds.), "Analysis of Cellular DNA or Abundance of mRNA by Radioactive In Situ Hybridization (RISH)," in *Methods in Gene Biotechnology*, pages 259-278 (CRC Press, Inc. 1997), and Wu et al. (eds.), "Localization of DNA or Abundance of mRNA by Fluorescence In Situ Hybridization (RISH)," in *Methods in Gene Biotechnology*, pages 279-289 (CRC Press, Inc. 1997)). Various additional diagnostic approaches are well-known to those of skill in the art (see, for example, Mathew (ed.), *Protocols in Human Molecular Genetics* (Humana Press, Inc. 1991), Coleman and Tsongalis, *Molecular Diagnostics* (Humana Press, Inc. 1996), and Elles, *Molecular Diagnosis of Genetic Diseases* (Humana Press, Inc., 1996)). Suitable test samples include blood, urine, saliva, tissue biopsy, and autopsy material.

The Zcytor14 gene resides in human chromosome 3p25-3p24. This region is associated with various disorders, including xeroderma pigmentosum, Marfan-like connective tissue disorder, cardiomyopathy, diabetes mellitus, Fanconi anemia, renal cell carcinoma, Marfan syndrome, Von Hippel-Lindau syndrome, and blepharophimosis. In addition, mutations of cytokine receptors are associated with particular diseases. For example, polymorphisms of cytokine receptors are associated with pulmonary alveolar proteinosis, familial periodic fever, and erythroleukemia. Thus, Zcytor14 nucleotide sequences can be used in linkage-based testing for various diseases, and to determine whether a subject's chromosomes contain a mutation in the Zcytor14 gene. Detectable chromosomal aberrations at the Zcytor14 gene locus include, but are not limited to, aneuploidy, gene copy number changes, insertions, deletions, restriction site changes and rearrangements. Of particular interest are genetic alterations that inactivate a Zcytor14 gene.

Aberrations associated with the Zcytor14 locus can be detected using nucleic acid molecules of the present invention by employing molecular genetic techniques, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine*, pages 83-88 (Humana Press, Inc. 1998)).

The protein truncation test is also useful for detecting the inactivation of a gene in which translation-terminating mutations produce only portions of the encoded protein (see, for example, Stoppa-Lyonnet et al., *Blood* 91:3920 (1998)). According to this approach, RNA is isolated from a biological sample, and used to synthesize cDNA. PCR is then used to amplify the Zcytor14 target sequence and to introduce an RNA polymerase promoter, a translation initiation sequence, and an in-frame ATG triplet. PCR products are transcribed using an RNA polymerase, and the transcripts are translated in vitro with a T7-coupled reticulocyte lysate system. The translation products are then fractionated by SDS-PAGE to determine the lengths of the translation products. The protein truncation test is described, for example, by Dracopoli et al. (eds.), *Current Protocols in Human Genetics*, pages 9.11.1-9.11.18 (John Wiley & Sons 1998).

The present invention also contemplates kits for performing a diagnostic assay for Zcytor14 gene expression or to detect mutations in the Zcytor14 gene. Such kits comprise nucleic acid probes, such as double-stranded nucleic acid molecules comprising the nucleotide sequence of SEQ ID NO:1 or SEQ ID NO:4, or a portion thereof, as well as single-stranded nucleic acid molecules having the complement of the nucleotide sequence of SEQ ID NO:1 or SEQ ID NO:4, or a portion thereof. Probe molecules may be DNA, RNA, oligonucleotides, and the like. Kits may comprise nucleic acid primers for performing PCR.

Such a kit can contain all the necessary elements to perform a nucleic acid diagnostic assay described above. A kit will comprise at least one container comprising a Zcytor14 probe or primer. The kit may also comprise a second container comprising one or more reagents capable of indicating the presence of Zcytor14 sequences. Examples of such indicator reagents include detectable labels such as radioactive labels, fluorochromes, chemiluminescent agents, and the like. A kit may also comprise a means for conveying to the user that the Zcytor14 probes and primers are used to detect Zcytor14 gene expression. For example, written instructions may state that the enclosed nucleic acid molecules can be used to detect either a nucleic acid molecule that encodes Zcytor14, or a nucleic acid molecule having a nucleotide sequence that is complementary to a Zcytor14-encoding nucleotide sequence. The written material can be applied directly to a container, or the written material can be provided in the form of a packaging insert.

11. Use of Anti-Zcytor14 Antibodies to Detect Zcytor14

The present invention contemplates the use of anti-Zcytor14 antibodies to screen biological samples in vitro for the presence of Zcytor14. In one type of in vitro assay, anti-Zcytor14 antibodies are used in liquid phase. For example, the presence of Zcytor14 in a biological sample can be tested by mixing the biological sample with a trace amount of labeled Zcytor14 and an anti-Zcytor14 antibody under conditions that promote binding between Zcytor14 and its antibody. Complexes of Zcytor14 and anti-Zcytor14 in the sample can be separated from the reaction mixture by contacting the complex with an immobilized protein which binds with the antibody, such as an Fc antibody or *Staphylococcus* protein A. The concentration of Zcytor14 in the biological sample will be inversely proportional to the amount of labeled Zcytor14 bound to the antibody and directly related to the amount of free labeled Zcytor14. Illustrative biological samples include blood, urine, saliva, tissue biopsy, and autopsy material.

Alternatively, in vitro assays can be performed in which anti-Zcytor14 antibody is bound to a solid-phase carrier. For example, antibody can be attached to a polymer, such as aminodextran, in order to link the antibody to an insoluble support such as a polymer-coated bead, a plate or a tube. Other suitable in vitro assays will be readily apparent to those of skill in the art.

In another approach, anti-Zcytor14 antibodies can be used to detect Zcytor14 in tissue sections prepared from a biopsy specimen. Such immunochemical detection can be used to determine the relative abundance of Zcytor14 and to determine the distribution of Zcytor14 in the examined tissue. General immunochemistry techniques are well established (see, for example, Ponder, "Cell Marking Techniques and Their Application," in *Mammalian Development: A Practical Approach*, Monk (ed.), pages 115-38 (IRL Press 1987), Coligan at pages 5.8.1-5.8.8, Ausubel (1995) at pages 14.6.1 to 14.6.13 (Wiley Interscience 1990), and Manson (ed.), *Methods In Molecular Biology, Vol. 10: Immunochemical Protocols* (The Humana Press, Inc. 1992)).

Immunochemical detection can be performed by contacting a biological sample with an anti-Zcytor14 antibody, and then contacting the biological sample with a detectably labeled molecule which binds to the antibody. For example, the detectably labeled molecule can comprise an antibody moiety that binds to anti-Zcytor14 antibody. Alternatively, the anti-Zcytor14 antibody can be conjugated with avidin/streptavidin (or biotin) and the detectably labeled molecule can comprise biotin (or avidin/streptavidin). Numerous variations of this basic technique are well-known to those of skill in the art.

Alternatively, an anti-Zcytor14 antibody can be conjugated with a detectable label to form an anti-Zcytor14 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3$H, $^{125}$I, $^{131}$I, $^{35}$S and $^{14}$C.

Anti-Zcytor14 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-Zcytor14 immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-Zcytor14 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-Zcytor14 immunoconjugates can be detectably labeled by linking an anti-Zcytor14 antibody component to an enzyme. When the anti-Zcytor14-enzyme conjugate is incubated in the presence of the appropriate substrate, the enzyme moiety reacts with the substrate to produce a chemical moiety, which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels, which can be employed in accordance with the present invention. The binding of marker moieties to anti-Zcytor14 antibodies can be accomplished using standard techniques known to the art. Typical methodology in this regard is described by Kennedy et al., *Clin. Chim. Acta* 70:1 (1976), Schurs et al., *Clin. Chim. Acta* 81:1 (1977), Shih et al., *Int'l J. Cancer* 46:1101 (1990), Stein et al, *Cancer Res.* 50:1330 (1990), and Coligan, supra.

Moreover, the convenience and versatility of immunochemical detection can be enhanced by using anti-Zcytor14 antibodies that have been conjugated with avidin, streptavidin, and biotin (see, for example, Wilchek et al. (eds.), "Avidin-Biotin Technology," *Methods In Enzymology, Vol.* 184 (Academic Press 1990), and Bayer et al., "Immunochemical Applications of Avidin-Biotin Technology," in *Methods In Molecular Biology, Vol.* 10, Manson (ed.), pages 149-162 (The Humana Press, Inc. 1992).

Methods for performing immunoassays are well-established. See, for example, Cook and Self, "Monoclonal Antibodies in Diagnostic Immunoassays," in *Monoclonal Antibodies: Production, Engineering, and Clinical Application*, Ritter and Ladyman (eds.), pages 180-208, (Cambridge University Press, 1995), Perry, "The Role of Monoclonal Antibodies in the Advancement of Immunoassay Technology," in *Monoclonal Antibodies: Principles and Applications*, Birch and Lennox (eds.), pages 107-120 (Wiley-Liss, Inc. 1995), and Diamandis, *Immunoassay* (Academic Press, Inc. 1996).

The present invention also contemplates kits for performing an immunological diagnostic assay for Zcytor14 gene expression. Such kits comprise at least one container comprising an anti-Zcytor14 antibody, or antibody fragment. A kit may also comprise a second container comprising one or more reagents capable of indicating the presence of Zcytor14 antibody or antibody fragments. Examples of such indicator reagents include detectable labels such as a radioactive label, a fluorescent label, a chemiluminescent label, an enzyme label, a bioluminescent label, colloidal gold, and the like. A kit may also comprise a means for conveying to the user that Zcytor14 antibodies or antibody fragments are used to detect Zcytor14 protein. For example, written instructions may state that the enclosed antibody or antibody fragment can be used to detect Zcytor14. The written material can be applied directly to a container, or the written material can be provided in the form of a packaging insert.

12. Therapeutic Uses of Polypeptides Having Zcytor14 Activity

The present invention includes the use of proteins, polypeptides, and peptides having Zcytor14 activity (such as Zcytor14 polypeptides (e.g., soluble forms of Zcytor14), Zcytor14 analogs (e.g., anti-Zcytor14 anti-idiotype antibodies), and Zcytor14 fusion proteins) to a subject who lacks an adequate amount of this polypeptide. In contrast, Zcytor14 antagonists (e.g., anti-Zcytor14 antibodies) can be used to treat a subject who produces an excess of Zcytor14.

As an illustration, Zcytor14 has an amino acid sequence that shares similarity with the human interleukin-17 receptor. Studies indicate that interleukin-17 plays a pivotal role in initiating or sustaining an inflammatory response (see, for example, Jovanovic et al., *J Immunol.* 160:3513 (1998)). Moreover, there is evidence that interleukin-17 activates the production of inflammatory mediators by synoviocytes, and that interleukin-17 contributes to the proinflammatory pattern that is characteristic of rheumatoid arthritis (Chabaud et al., *J Immunol.* 161:409 (1998); Chabaud et al., *Arthritis Rheum.* 42:963 (1999)). Accordingly, polypeptides having Zcytor14 activity (e.g., Zcytor14 polypeptides, functional fragments of Zcytor14 including a soluble Zcytor14 receptor, anti-Zcytor14 anti-idiotype antibodies, etc.) can be used to treat inflammation, and conditions, such as rheumatoid arthritis, that are associated with inflammation.

Generally, the dosage of administered Zcytor14 (or Zcytor14 analog or fusion protein) will vary depending upon such factors as the patient's age, weight, height, sex, general medical condition and previous medical history. Typically, it is desirable to provide the recipient with a dosage of Zcytor14 polypeptide, which is in the range of from about 1 pg/kg to 10 mg/kg (amount of agent/body weight of patient), although a lower or higher dosage also may be administered as circumstances dictate.

Administration of a Zcytor14 polypeptide to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising Zcytor14 can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science* 269:850 (1995)). Transdermal delivery using electroporation provides another means to administer a molecule having Zcytor14 binding activity (Potts et al., *Pharm. Biotechnol.* 10:213 (1997)).

A pharmaceutical composition comprising a protein, polypeptide, or peptide having Zcytor14 binding activity can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences*, 19th Edition (Mack Publishing Company 1995).

For purposes of therapy, molecules having Zcytor14 binding activity and a pharmaceutically acceptable carrier are administered to a patient in a therapeutically effective amount. A combination of a protein, polypeptide, or peptide having Zcytor14 binding activity and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response.

A pharmaceutical composition comprising Zcytor14 (or Zcytor14 analog or fusion protein) can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):S61 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 µm) are typically taken up by cells of the reticuloendothelial system, located principally in the liver and spleen, whereas liposomes larger than 3.0 µm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

Polypeptides having Zcytor14 binding activity can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in Liposome Technology, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified polypeptides having binding Zcytor14 activity and Zcytor14 antagonists, in which a polypeptide is linked with a polymer, as discussed above.

Other dosage forms can be devised by those skilled in the art, as shown, for example, by Ansel and Popovich, *Pharmaceutical Dosage Forms and Drug Delivery Systems,* 5$^{th}$ Edition (Lea & Febiger 1990), Gennaro (ed.), *Remington's Pharmaceutical Sciences,* 19$^{th}$ Edition (Mack Publishing Company 1995), and by Ranade and Hollinger, *Drug Delivery Systems* (CRC Press 1996).

As an illustration, pharmaceutical compositions may be supplied as a kit comprising a container that comprises a polypeptide with a Zcytor14 extracellular domain or a Zcytor14 antagonist (e.g., an antibody or antibody fragment that binds a Zcytor14 polypeptide). Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the Zcytor14 composition is contraindicated in patients with known hypersensitivity to Zcytor14.

13. Therapeutic Uses of Zcytor14 Nucleotide Sequences

The present invention includes the use of Zcytor14 nucleotide sequences to provide Zcytor14 to a subject in need of such treatment. In addition, a therapeutic expression vector can be provided that inhibits Zcytor14 gene expression, such as an anti-sense molecule, a ribozyme, or an external guide sequence molecule.

There are numerous approaches to introduce a Zcytor14 gene to a subject, including the use of recombinant host cells that express Zcytor14, delivery of naked nucleic acid encoding Zcytor14, use of a cationic lipid carrier with a nucleic acid molecule that encodes Zcytor14, and the use of viruses that express Zcytor14, such as recombinant retroviruses, recombinant adeno-associated viruses, recombinant adenoviruses, and recombinant Herpes simplex viruses (see, for example, Mulligan, *Science* 260:926 (1993), Rosenberg et al., *Science* 242:1575 (1988), LaSalle et al., *Science* 259:988 (1993), Wolff et al., *Science* 247:1465 (1990), Breakfield and Deluca, *The New Biologist* 3:203 (1991)). In an ex vivo approach, for example, cells are isolated from a subject, transfected with a vector that expresses a Zcytor14 gene, and then transplanted into the subject.

In order to effect expression of a Zcytor14 gene, an expression vector is constructed in which a nucleotide sequence encoding a Zcytor14 gene is operably linked to a core promoter, and optionally a regulatory element, to control gene transcription. The general requirements of an expression vector are described above.

Alternatively, a Zcytor14 gene can be delivered using recombinant viral vectors, including for example, adenoviral vectors (e.g., Kass-Eisler et al., *Proc. Nat'l Acad. Sci. USA* 90:11498 (1993), Kolls et al., *Proc. Nat'l Acad. Sci. USA* 91:215 (1994), Li et al., *Hum. Gene Ther.* 4:403 (1993), Vincent et al., *Nat. Genet.* 5:130 (1993), and Zabner et al., *Cell* 75:207 (1993)), adenovirus-associated viral vectors (Flotte et al., *Proc. Nat'l Acad. Sci. USA* 90:10613 (1993)), alphaviruses such as Semliki Forest Virus and Sindbis Virus (Hertz and Huang, *J. Vir.* 66:857 (1992), Raju and Huang, *J. Vir.* 65:2501 (1991), and Xiong et al., *Science* 243:1188 (1989)), herpes viral vectors (e.g., U.S. Pat. Nos. 4,769,331, 4,859,587, 5,288,641 and 5,328,688), parvovirus vectors (Koering et al., *Hum. Gene Therap.* 5:457 (1994)), pox virus vectors (Ozaki et al., *Biochem. Biophys. Res. Comm.* 193:653 (1993), Panicali and Paoletti, *Proc. Nat'l Acad. Sci. USA* 79:4927 (1982)), pox viruses, such as canary pox virus or vaccinia virus (Fisher-Hoch et al., *Proc. Nat'l Acad. Sci. USA* 86:317 (1989), and Flexner et al., *Ann. N.Y. Acad. Sci.* 569:86 (1989)), and retroviruses (e.g., Baba et al., *J. Neurosurg* 79:729 (1993), Ram et al., *Cancer Res.* 53:83 (1993), Takamiya et al., *J. Neurosci. Res* 33:493 (1992), Vile and Hart, *Cancer Res.* 53:962 (1993), Vile and Hart, *Cancer Res.* 53:3860 (1993), and Anderson et al., U.S. Pat. No. 5,399,346). Within various embodiments, either the viral vector itself, or a viral particle, which contains the viral vector may be utilized in the methods and compositions described below.

As an illustration of one system, adenovirus, a double-stranded DNA virus, is a well-characterized gene transfer vector for delivery of a heterologous nucleic acid molecule (for a review, see Becker et al., *Meth. Cell Biol.* 43:161 (1994); Douglas and Curiel, *Science & Medicine* 4:44 (1997)). The adenovirus system offers several advantages including: (i) the ability to accommodate relatively large DNA inserts, (ii) the ability to be grown to high-titer, (iii) the ability to infect a broad range of mammalian cell types, and (iv) the ability to be used with many different promoters including ubiquitous, tissue specific, and regulatable promoters. In addition, adenoviruses can be administered by intravenous injection, because the viruses are stable in the bloodstream.

Using adenovirus vectors where portions of the adenovirus genome are deleted, inserts are incorporated into the viral DNA by direct ligation or by homologous recombination with a co-transfected plasmid. In an exemplary system, the essential E1 gene is deleted from the viral vector, and the virus will not replicate unless the E1 gene is provided by the host cell. When intravenously administered to intact animals, adenovirus primarily targets the liver. Although an adenoviral delivery system with an E1 gene deletion cannot replicate in the host cells, the host's tissue will express and process an encoded heterologous protein. Host cells will also secrete the heterologous protein if the corresponding gene includes a secretory signal sequence. Secreted proteins will enter the circulation from tissue that expresses the heterologous gene (e.g., the highly vascularized liver).

Moreover, adenoviral vectors containing various deletions of viral genes can be used to reduce or eliminate immune responses to the vector. Such adenoviruses are E1-deleted, and in addition, contain deletions of E2A or E4 (Lusky et al., *J. Virol.* 72:2022 (1998); Raper et al., *Human Gene Therapy* 9:671 (1998)). The deletion of E2b has also been reported to reduce immune responses (Amalfitano et al., *J. Virol.* 72:926 (1998)). By deleting the entire adenovirus genome, very large inserts of heterologous DNA can be accommodated. Generation of so called "gutless" adenoviruses, where all viral genes are deleted, are particularly advantageous for insertion of large inserts of heterologous DNA (for a review, see Yeh. and Perricaudet, *FASEB J.* 11:615 (1997)).

High titer stocks of recombinant viruses capable of expressing a therapeutic gene can be obtained from infected mammalian cells using standard methods. For example, recombinant herpes simplex virus can be prepared in Vero cells, as described by Brandt et al., *J. Gen. Virol.* 72:2043 (1991), Herold et al., *J. Gen. Virol.* 75:1211 (1994), Visalli and Brandt, *Virology* 185:419 (1991), Grau et al., *Invest. Ophthalmol. Vis. Sci.* 30:2474 (1989), Brandt et al., *J. Virol. Meth.* 36:209 (1992), and by Brown and MacLean (eds.), *HSV Virus Protocols* (Humana Press 1997).

Alternatively, an expression vector comprising a Zcytor14 gene can be introduced into a subject's cells by lipofection in vivo using liposomes. Synthetic cationic lipids can be used to prepare liposomes for in vivo transfection of a gene encoding a marker (Felgner et al., *Proc. Nat'l Acad. Sci. USA* 84:7413 (1987); Mackey et al., *Proc. Nat'l Acad. Sci. USA* 85:8027 (1988)). The use of lipofection to introduce exogenous genes into specific organs in vivo has certain practical advantages. Liposomes can be used to direct transfection to particular cell types, which is particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Electroporation is another alternative mode of administration. For example, Aihara and Miyazaki, *Nature Biotechnology* 16:867 (1998), have demonstrated the use of in vivo electroporation for gene transfer into muscle.

In an alternative approach to gene therapy, a therapeutic gene may encode a Zcytor14 anti-sense RNA that inhibits the expression of Zcytor14. Suitable sequences for anti-sense molecules can be derived from the nucleotide sequences of Zcytor14 disclosed herein.

Alternatively, an expression vector can be constructed in which a regulatory element is operably linked to a nucleotide sequence that encodes a ribozyme. Ribozymes can be designed to express endonuclease activity that is directed to a certain target sequence in a mRNA molecule (see, for example, Draper and Macejak, U.S. Pat. No. 5,496,698, McSwiggen, U.S. Pat. No. 5,525,468, Chowrira and McSwiggen, U.S. Pat. No. 5,631,359, and Robertson and Goldberg, U.S. Pat. No. 5,225,337). In the context of the present invention, ribozymes include nucleotide sequences that bind with Zcytor14 mRNA.

In another approach, expression vectors can be constructed in which a regulatory element directs the production of RNA transcripts capable of promoting RNase P-mediated cleavage of mRNA molecules that encode a Zcytor14 gene. According to this approach, an external guide sequence can be constructed for directing the endogenous ribozyme, RNase P, to a particular species of intracellular mRNA, which is subsequently cleaved by the cellular ribozyme (see, for example, Altman et al., U.S. Pat. No. 5,168,053, Yuan et al., *Science* 263:1269 (1994), Pace et al., international publication No. WO 96/18733, George et al., international publication No. WO 96/21731, and Werner et al., international publication No. WO 97/33991). Preferably, the external guide sequence comprises a ten to fifteen nucleotide sequence complementary to Zcytor14 mRNA, and a 3'-NCCA nucleotide sequence, wherein N is preferably a purine. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

In general, the dosage of a composition comprising a therapeutic vector having a Zcytor14 nucleotide sequence, such as a recombinant virus, will vary depending upon such factors as the subject's age, weight, height, sex, general medical condition and previous medical history. Suitable routes of administration of therapeutic vectors include intravenous injection, intraarterial injection, intraperitoneal injection, intramuscular injection, intratumoral injection, and injection into a cavity that contains a tumor. As an illustration, Horton et al., *Proc. Nat'l Acad. Sci. USA* 96:1553 (1999), demonstrated that intramuscular injection of plasmid DNA encoding interferon-α produces potent antitumor effects on primary and metastatic tumors in a murine model.

A composition comprising viral vectors, non-viral vectors, or a combination of viral and non-viral vectors of the present invention can be formulated according to known methods to prepare pharmaceutically useful compositions, whereby vectors or viruses are combined in a mixture with a pharmaceutically acceptable carrier. As noted above, a composition, such as phosphate-buffered saline is said to be a "pharmaceutically acceptable carrier" if its administration can be tolerated by a recipient subject. Other suitable carriers are well-known to those in the art (see, for example, *Remington's Pharmaceutical Sciences*, 19th Ed. (Mack Publishing Co. 1995), and *Gilman's the Pharmacological Basis of Therapeutics*, 7th Ed. (MacMillan Publishing Co. 1985)).

For purposes of therapy, a therapeutic gene expression vector, or a recombinant virus comprising such a vector, and a pharmaceutically acceptable carrier are administered to a subject in a therapeutically effective amount. A combination of an expression vector (or virus) and a pharmaceutically acceptable carrier is said to be administered in a "therapeutically effective amount" if the amount administered is physiologically significant. An agent is physiologically significant if its presence results in a detectable change in the physiology of a recipient subject. For example, an agent used to treat inflammation is physiologically significant if its presence alleviates the inflammatory response.

When the subject treated with a therapeutic gene expression vector or a recombinant virus is a human, then the therapy is preferably somatic cell gene therapy. That is, the preferred treatment of a human with a therapeutic gene expression vector or a recombinant virus does not entail introducing into cells a nucleic acid molecule that can form part of a human germ line and be passed onto successive generations (i.e., human germ line gene therapy).

14. Production of Transgenic Mice

Transgenic mice can be engineered to over-express the Zcytor14 gene in all tissues or under the control of a tissue-specific or tissue-preferred regulatory element. These over-producers of Zcytor14 can be used to characterize the phenotype that results from over-expression, and the transgenic animals can serve as models for human disease caused by excess Zcytor14. Transgenic mice that over-express Zcytor14 also provide model bioreactors for production of Zcytor14, such as soluble Zcytor14, in the milk or blood of larger animals. Methods for producing transgenic mice are well-known to those of skill in the art (see, for example, Jacob, "Expression and Knockout of Interferons in Transgenic Mice," in *Overexpression and Knockout of Cytokines in Transgenic Mice*, Jacob (ed.), pages 111-124 (Academic Press, Ltd. 1994), Monastersky and Robl (eds.), *Strategies in Transgenic Animal Science* (ASM Press 1995), and Abbud and Nilson, "Recombinant Protein Expression in Transgenic Mice," in *Gene Expression Systems: Using Nature for the Art of Expression*, Fernandez and Hoeffler (eds.), pages 367-397 (Academic Press, Inc. 1999)).

For example, a method for producing a transgenic mouse that expresses a Zcytor14 gene can begin with adult, fertile males (studs) (B6C3f1, 2-8 months of age (Taconic Farms, Germantown, N.Y.)), vasectomized males (duds) (B6D2f1, 2-8 months, (Taconic Farms)), prepubescent fertile females (donors) (B6C3f1, 4-5 weeks, (Taconic Farms)) and adult fertile females (recipients) (B6D2f1, 2-4 months, (Taconic Farms)). The donors are acclimated for one week and then injected with approximately 8 IU/mouse of Pregnant Mare's Serum gonadotrophin (Sigma Chemical Company; St. Louis, Mo.) I.P., and 46-47 hours later, 8 IU/mouse of human Chorionic Gonadotropin (hCG (Sigma)) I.P. to induce superovulation. Donors are mated with studs subsequent to hormone injections. Ovulation generally occurs within 13 hours of hCG injection. Copulation is confirmed by the presence of a vaginal plug the morning following mating.

Fertilized eggs are collected under a surgical scope. The oviducts are collected and eggs are released into urinanalysis slides containing hyaluronidase (Sigma). Eggs are washed once in hyaluronidase, and twice in Whitten's W640 medium (described, for example, by Menino and O'Claray, *Biol. Reprod.* 77:159 (1986), and Dienhart and Downs, *Zygote* 4:129 (1996)) that has been incubated with 5% $CO_2$, 5%° 2' and 90% $N_2$ at 37° C. The eggs are then stored in a 37° C./5% $CO_2$ incubator until microinjection.

Ten to twenty micrograms of plasmid DNA containing a Zcytor14 encoding sequence is linearized, gel-purified, and resuspended in 10 mM Tris-HCl (pH 7.4), 0.25 mM EDTA (pH 8.0), at a final concentration of 5-10 nanograms per microliter for microinjection. For example, the Zcytor14 encoding sequences can encode a polypeptide comprising amino acid residues 21 to 452 of SEQ ID NO:2.

Plasmid DNA is microinjected into harvested eggs contained in a drop of W640 medium overlaid by warm, $CO_2$-equilibrated mineral oil. The DNA is drawn into an injection needle (pulled from a 0.75 mm ID, 1 mm OD borosilicate glass capillary), and injected into individual eggs. Each egg is penetrated with the injection needle, into one or both of the haploid pronuclei.

Picoliters of DNA are injected into the pronuclei, and the injection needle withdrawn without coming into contact with the nucleoli. The procedure is repeated until all the eggs are injected. Successfully microinjected eggs are transferred into an organ tissue-culture dish with pre-gassed W640 medium for storage overnight in a 37° C./5% $CO_2$ incubator.

The following day, two-cell embryos are transferred into pseudopregnant recipients. The recipients are identified by the presence of copulation plugs, after copulating with vasectomized duds. Recipients are anesthetized and shaved on the dorsal left side and transferred to a surgical microscope. A small incision is made in the skin and through the muscle wall in the middle of the abdominal area outlined by the ribcage, the saddle, and the hind leg, midway between knee and spleen. The reproductive organs are exteriorized onto a small surgical drape. The fat pad is stretched out over the surgical drape, and a baby serrefine (Roboz, Rockville, Md.) is attached to the fat pad and left hanging over the back of the mouse, preventing the organs from sliding back in.

With a fine transfer pipette containing mineral oil followed by alternating W640 and air bubbles, 12-17 healthy two-cell embryos from the previous day's injection are transferred into the recipient. The swollen ampulla is located and holding the oviduct between the ampulla and the bursa, a nick in the oviduct is made with a 28 g needle close to the bursa, making sure not to tear the ampulla or the bursa.

The pipette is transferred into the nick in the oviduct, and the embryos are blown in, allowing the first air bubble to escape the pipette. The fat pad is gently pushed into the peritoneum, and the reproductive organs allowed to slide in. The peritoneal wall is closed with one suture and the skin closed with a wound clip. The mice recuperate on a 37° C. slide warmer for a minimum of four hours.

The recipients are returned to cages in pairs, and allowed 19-21 days gestation. After birth, 19-21 days postpartum is allowed before weaning. The weanlings are sexed and placed into separate sex cages, and a 0.5 cm biopsy (used for genotyping) is snipped off the tail with clean scissors.

Genomic DNA is prepared from the tail snips using, for example, a QIAGEN DNEASY kit following the manufacturer's instructions. Genomic DNA is analyzed by PCR using primers designed to amplify a Zcytor14 gene or a selectable marker gene that was introduced in the same plasmid. After animals are confirmed to be transgenic, they are back-crossed into an inbred strain by placing a transgenic female with a wild-type male, or a transgenic male with one or two wild-type female(s). As pups are born and weaned, the sexes are separated, and their tails snipped for genotyping.

To check for expression of a transgene in a live animal, a partial hepatectomy is performed. A surgical prep is made of the upper abdomen directly below the zyphoid process. Using sterile technique, a small 1.5-2 cm incision is made below the sternum and the left lateral lobe of the liver exteriorized. Using 4-0 silk, a tie is made around the lower lobe securing it outside the body cavity. An atraumatic clamp is used to hold the tie while a second loop of absorbable Dexon (American Cyanamid; Wayne, N.J.) is placed proximal to the first tie. A distal cut is made from the Dexon tie and approximately 100 mg of the excised liver tissue is placed in a sterile petri dish. The excised liver section is transferred to a 14 ml polypropylene round bottom tube and snap frozen in liquid nitrogen and then stored on dry ice. The surgical site is closed with suture and wound clips, and the animal's cage placed on a 37° C. heating pad for 24 hours post operatively. The animal is checked daily post operatively and the wound clips removed 7-10 days after surgery. The expression level of Zcytor14 mRNA is examined for each transgenic mouse using an RNA solution hybridization assay or polymerase chain reaction.

In addition to producing transgenic mice that over-express Zcytor14, it is useful to engineer transgenic mice with either abnormally low or no expression of the gene. Such transgenic mice provide useful models for diseases associated with a lack of Zcytor14. As discussed above, Zcytor14 gene expression can be inhibited using anti-sense genes, ribozyme genes, or external guide sequence genes. To produce transgenic mice that under-express the Zcytor14 gene, such inhibitory sequences are targeted to Zcytor14 mRNA. Methods for producing transgenic mice that have abnormally low expression of a particular gene are known to those in the art (see, for example, Wu et al., "Gene Underexpression in Cultured Cells and Animals by Antisense DNA and RNA Strategies," in *Methods in Gene Biotechnology*, pages 205-224 (CRC Press 1997)).

An alternative approach to producing transgenic mice that have little or no Zcytor14 gene expression is to generate mice having at least one normal Zcytor14 allele replaced by a nonfunctional Zcytor14 gene. One method of designing a nonfunctional Zcytor14 gene is to insert another gene, such as a selectable marker gene, within a nucleic acid molecule that encodes Zcytor14. Standard methods for producing these so-called "knockout mice" are known to those skilled in the art (see, for example, Jacob, "Expression and Knockout of Interferons in Transgenic Mice," in *Overexpression and Knockout of Cytokines in Transgenic Mice*, Jacob (ed.), pages 111-124 (Academic Press, Ltd. 1994), and Wu et al., "New Strategies for Gene Knockout," in *Methods in Gene Biotechnology*, pages 339-365 (CRC Press 1997)).

The present invention, thus generally described, will be understood more readily by reference to the following example, which is provided by way of illustration and is not intended to be limiting of the present invention.

EXAMPLE 1

Expression of the Zcytor14 Gene

Northern analyses were performed using Human Multiple Tissue Blots (CLONTECH Laboratories, Inc., Palo Alto, Calif.). Two probes were generated from gel purified PCR products. The first probe was made using ZC21798 (5' CGG CGT GGT GGT CTT GCT CTT 3'; SEQ ID NO:8) and ZC21808 (5' TCC CGT CCC CCG CCC CAG GTC 3'; SEQ ID NO:9) as primers. The probe was a radioactively labeled using the Multiprime labeling kit from Amersham (Arlington Heights, Ill.) according to the manufacturer's protocol. The probe was purified using a NUCTRAP push column (STRATAGENE, La Jolla, Calif.). EXPRESSHYB (CLONTECH) solution was used for the prehybridization and hybridization solutions for the northern blots. Hybridization took place overnight at 65□C. Following hybridization, the blots were washed for 30 minutes each in solutions that contained 0.1% SDS and SSC as follows: twice in 2×SSC at room temperature, three times in 0.1×SSC at 50□C, once in 0.1×SSC at 55□C, and once in 0.1×SSC at 65□C. The results demonstrated the Zcytor14 gene is strongly expressed in thyroid, adrenal gland, prostate, and liver tissues, and expressed to a lesser extent in heart, small intestine, stomach, and trachea tissues. In contrast, there is little or no expression in brain, placenta, lung, skeletal muscle, kidney, pancreas, spleen, thymus, testis, ovary, colon, peripheral blood leukocytes, spinal cord, lymph node, and bone marrow.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polypeptide comprising amino acid residues 21 to 452 of SEQ ID NO:2.

2. A fusion protein comprising:
   amino acid residues 21 to 452 of SEQ ID NO:2; and
   an immunoglobulin heavy chain constant region.

3. The fusion protein of claim 2, wherein the immunoglobulin heavy chain constant region is an $F_c$ fragment.

4. The fusion protein of claim 3, wherein the $F_c$ fragment is a human $F_c$ fragment.

5. An isolated polypeptide comprising at least 4 contiguous amino acid residues of SEQ ID NO:2.

6. The polypeptide of claim 5, which is a fusion polypeptide further comprising an immunoglobulin polypeptide or a maltose binding protein.

7. An immunogenic composition comprising the polypeptide of claim 5 or 6.

* * * * *

UNITED STATES PATENT AND TRADEMARK OFFICE
CERTIFICATE OF CORRECTION

PATENT NO. : 7,517,958 B2
APPLICATION NO. : 11/537916
DATED : April 14, 2009
INVENTOR(S) : Scott R. Presnell et al.

Page 1 of 1

It is certified that error appears in the above-identified patent and that said Letters Patent is hereby corrected as shown below:

Column 12, line 66 "O-globin" should read --β-globin--
Column 13, line 11 "110%" should read --±10%--
Column 13, line 45 "Poly(A) RNA" should read --Poly(A) +RNA--
Column 26, line 3 "JS1R-TNO" should read --IS1R-TNO--
Column 27, lines 15-16 "SEQ ID NO:1" should read --SEQ ID NO:11--
Column 30, line 6 "Sj21AE, and Sj21" should read --Sf21AE, and Sf21--
Column 30, line 11 "Sf00" should read --Sf900--
Column 31, lines 5-6 "Acremonim chrysogen m" should read --Acremonium chrysogenum--
Column 33, line 11 "Muir et a," should read --Muir et al,--
Column 33, line 58 "Kauffiman" should read --Kauffman--
Column 35, line 30 "□" should read --ε--
Column 38, lines 51-52 "lysine 8-amino" should read --lysine ε-amino--
Column 43, line 9 "mono-clonal" should be --monoclonal--
Column 58, line 50 "5%° 2'" should read --5% $O_2$--
Column 60, line 50 "65□C" should read --65°C--
Column 60, line 54 "50□C" should read --50°C--
Column 60, line 55 "55□C" should read --55°C--
Column 92, lines 46-47, Claim 5 should read --An isolated polypeptide comprising at least 100 contiguous amino acid residues of the polypeptide consisting of amino acid residues 21-452 of SEQ ID NO:2.--

Signed and Sealed this

Third Day of November, 2009

David J. Kappos
*Director of the United States Patent and Trademark Office*